United States Patent [19]

Isobe

[11] Patent Number: 5,096,298

[45] Date of Patent: Mar. 17, 1992

[54] METHOD FOR MEASURING REFRACTIVE INDEX OF THIN FILM LAYER

[75] Inventor: Tami Isobe, Yokohama, Japan

[73] Assignee: Ricoh Company, Ltd., Tokyo, Japan

[21] Appl. No.: 453,902

[22] Filed: Dec. 20, 1989

Related U.S. Application Data

[63] Continuation-in-part of Ser. No. 256,991, Oct. 13, 1988.

[30] Foreign Application Priority Data

Feb. 5, 1988 [JP] Japan .................... 63-25128
Sep. 12, 1988 [JP] Japan .................... 63-228199
Sep. 12, 1988 [JP] Japan .................... 63-228200

[51] Int. Cl.$^5$ .................................... G01J 4/00
[52] U.S. Cl. .................................... 356/369; 356/361
[58] Field of Search .................................... 356/361, 369

[56] References Cited

PUBLICATIONS

Ruiz-Urbieta et al., "Methods for Determining Film Thickness and Optical Constants of Films and Substrates", *J. Opt. Soc. Amer.*, vol. 61, pp. 351–359, 3/1971.

*Primary Examiner*—Samuel Turner
*Attorney, Agent, or Firm*—Oblon, Spivak, McClelland, Maier & Neustadt

[57] ABSTRACT

A method for measuring refractive index of a thin film layer formed on the other layer having a known refractive index includes following steps. A step of irradiating P-polarized monochromatic light and S-polarized monochromatic light individually on the thin film layer with a prescribed angle of incidence, a step of determining reflectances $R_p$ and $R_s$ for the P-polarized monochromatic light and S-polarized monochromatic light, respectively, by detecting luminous intensity of reflected light from the thin film layer, and a step of specifying the refractive index of the thin film layer by prescribed calculation either using the amount of phase changes produced by reflection of said P-polarized light and S-polarized light on a boundary surface between the thin film layer and the medium, the phase changes being determined in accordance with the refractive index of the medium and the reflectances $R_p$ and $R_s$, or using the amount of phase changes of lights during propagation from an upper surface of the thin film layer to a lower surface thereof the phase changes being determined in accordance with the refractive index of the medium and the reflectances $R_p$ and $R_s$.

2 Claims, 9 Drawing Sheets

METHOD FOR MEASURING REFRACTIVE INDEX OF THIN FILM LAYER

CROSS-REFERENCES TO RELATED APPLICATION

This application is a Continuation-in-part application of U.S. Ser. No. 07/256,991 filed on Oct. 13, 1988, now allowed.

BACKGROUND OF THE INVENTION

The present invention relates to a method for measuring refractive index of a thin film layer formed on medium having a known refractive index.

In the optical engineering field, it is often necessary to measure refractive index of a thin film. It is known to use a polarization analysis method as a noncontact and nondestructive measuring method. However, the ellipsometry method requires a complicated huge apparatus.

In order to conveniently, readily and accurately measure the refractive index of a thin film layer, the applicant of this application proposed a measuring method in Japanese Patent Application Nos. 61-282758 and 61-287495 which disclose a method for measuring refractive index of a thin film layer formed on a substrate having a known refractive index wherein P-polarized monochromatic light and S-polarized monochromatic light are irradiated to the thin film at a predetermined angle of incidence and reflectances Rp and Rs for the P-polarized monochromatic light and the S-polarized monochromatic light are detected and wherein the refractive index of the thin film layer is calculated using the known refractive index of the substrate and the reflectances Rp and Rs in accordance with a predetermined sequence.

However, the proposed method does not consider the absorption effect of the substrate, therefore it can be applied only to a dielectric substrate but cannot be applied to an absorbent substrate unless a compensation process is added.

Also, the proposed method is applied only to a monolayered film and cannot be applied to a multi-layered film.

SUMMARY OF THE INVENTION

The present invention was made considering the above-mentioned points. A first object of the present invention is to provide a novel method for measuring refractive index of a thin film layer, wherein the refractive index can be conveniently, readily and accurately measured and wherein the absorption of the substrate is considered so that the invention can be applied to an absorbent substrate as well as to a dielectric substrate.

A second object of the present invention is to improve the above-mentioned proposed method so as to provide a novel method for measuring refractive index of an uppermost layer of a multi-layered thin film formed on a substrate.

In order to achieve the first object, in accordance with the present invention, there is provided a method for measuring refractive index of a thin film layer wherein P-polarized monochromatic light and S-polarized monochromatic light are irradiated with a predetermined angle of incidence to a thin film layer formed on medium having a known refractive index and reflectances Rp and Rs for the P-polarized monochromatic light and the S-polarized monochromatic light are detected, then the refractive index of the thin film layer is specified by prescribed calculation either using the amount of phase changes produced by the reflection of the P-polarized light and S-polarized light on a boundary surface between the thin film layer and the medium, which phase changes are determined in accordance with the refractive index of the medium and the reflectances Rp and Rs, or using the amount of phase changes of lights during propagation from an upper surface of the thin film layer to a lower surface thereof, which phase changes are determined in accordance with the refractive index of the medium and the reflectances Rp and Rs.

In order to achieve the first object, more particularly, there is provided a method for measuring refractive index of a thin film layer wherein P-polarized monochromatic light and S-polarized monochromatic light are irradiated with a predetermined angle of incidence to a thin film layer formed on a substrate having a known refractive index $\eta_3$ and reflectances Rp and Rs for the P-polarized monochromatic light and the S-polarized monochromatic light are detected, then $(\phi_{23p} - \phi_{23S})$ which is the difference between the phase change of the P-polarized light of the interface and that of the S-polarized light is calculated in accordance with the refractive index $\eta_3^*$ of the substrate and the reflectances Rp and Rs, using the assumptive values of the refractive index $n_2$ of the thin film, on the other hand, the value of $(\phi_{23p} - \phi_{23S})$ is also calculated in accordance with the refractive index $\eta_3^*$ and assumptive values of the refractive index $n_2$ using the following equations, $$\tan \phi_{23p} = \frac{2n_2 n_3^2 \cos\theta_2 (2k_3 u_3 - (1-k_3^2) v_3)}{n_3^4 (1+k_3^2)^2 \cos^2\theta_2 - n_2^2 (u_3^2 + v_3^2)} \equiv \xi_p(n_2)$$

$$\tan \phi_{23s} = \frac{2 v_3 n_2 \cos\theta_2}{u_3^2 + v_3^2 - n_2^2 \cos^2\theta_2} \equiv \xi_s(n_2)$$

wherein $$2u_3^2 = n_3^2(1-k_3^2) - n_1^2 \sin^2\theta_1 + \sqrt{(n_3^2(1-k_3^2) - n_1^2 \sin^2\theta_1)^2 + 4n_3^4 k_3^2}$$

$$2v_3^2 = -n_3^2(1-k_3^2) + n_1^2 \sin^2\theta_1 + \sqrt{(n_3^2(1-k_3^2) - n_1^2 \sin^2\theta_1)^2 + 4n_3^4 k_3^2}$$

$n_1$: refractive index of ambient medium (usually air having $n_1 = 1$)
$\theta_1$: angle of incidence of light to thin film layer,
after that the value of $\cos^{-1}\{\eta_p(n_2)\} - \cos^{-1}\{\eta_s(n_2)\}$ and the value of $\tan^{-1}\{\xi_p(n_2)\} - \tan^{-1}\{\xi_s(n_2)\}$ are compared and the value of $n_2$ which makes both values equal is determined as the genuine refractive index of the thin film.

In order to achieve the first object, particularly, there is further provided a method for measuring refractive index of a thin film wherein P-polarized monochromatic light and S-polarized monochromatic light are irradiated with a predetermined angle of incidence to a thin film formed on a substrate having a known refractive index $n_3^* = n_3(1 + ik_3)$ and reflectances Rp and Rs for the P-polarized monochromatic light and the S-polarized monochromatic light are detected, then $\cos(\phi_{23p} + 2\beta)$ and $\cos(\phi_{23S} + 2\beta)$ are determined in accordance with the refractive index $n_3^*$ and the reflectances Rp, Rs using Fresnel equations as a function of only one variable (refractive index $n_2$) of the thin film as follows, $$\cos(\phi_{23p}+2\beta)=\eta_p(n_2)$$

$$\cos(\phi_{23S}+2\beta)=\eta_s(n_2)$$

wherein, $\phi_{23p}$, $\phi_{23S}$: phase change amount of P-polarized light and S-polarized light reflected on the boundary surface between the thin film and the substrate, $2\beta$: phase change amount of light during propagation from an upper surface of the thin film to a lower surface thereof and back to the upper surface.

On the other hand, tan $\phi_{23p}$ and tan $\phi_{23S}$ are determined in accordance with the refractive index of the thin film as a function of only one variable (the refractive index $n_2$) of the thin film, using the following equations, $$\tan\phi_{23p} = \frac{2n_2n_3^2\cos\theta_2(2k_3u_3 - (1-k_3^2)v_3)}{n_3^4(1+k_3^2)^2\cos^2\theta_2 - n_2^2(u_3^2+v_3^2)}$$

$$\tan\phi_{23s} = \frac{2v_3n_2\cos\theta_2}{u_3^2+v_3^2-n_2^2\cos^2\theta_2}$$

wherein $$2u_3^2 = n_3^2(1-k_3^2) - n_1^2\sin^2\theta_1 + \sqrt{(n_3^2(1-k_3^2) - n_1^2\sin^2\theta_1)^2 + 4n_3^4k_3^2}$$

$$2v_3^2 = -n_3^2(1-k_3^2) + n_1^2\sin^2\theta_1 + \sqrt{(n_3^2(1-k_3^2) - n_1^2\sin^2\theta_1)^2 + 4n_3^4k_3^2}$$

$n_1$: refractive index of ambient medium (usually air in which $n_1=1$)

$\theta_1$: angle of incidence of light to thin film.

In order to achieve the second object, in accordance with the present invention, there is provided a method for measuring refractive index of an uppermost thin film layer of a multi-layered thin film formed on a substrate having a known refractive index wherein the refractive index and thickness of the layers other than the uppermost layer are known, in which P-polarized monochromatic light and S-polarized monochromatic light are irradiated at a predetermined angle of incidence to the uppermost thin film and reflectances Rp and Rs for the P-polarized monochromatic light and the S-polarized monochromatic light are detected.

In order to achieve the second object, the present invention further provides a method for measuring refractive index of an uppermost layer film of a plurality of thin film layers formed on a substrate having a known refractive index, wherein the refractive indices of the thin film layers other than the uppermost film and the thickness thereof are known, the method comprising a detection step for measuring reflectances, a specifying step for specifying functions for calculation and a calculation step.

In the detection step, P-polarized monochromatic light and S-polarized monochromatic light are irradiated to the thin film layers on the substrate, and reflectances Rp and Rs for the P-polarized monochromatic light and the S-polarized monochromatic light are detected. The calculational function specifying step comprises a first sub-step wherein $\eta_p(n_2)$ and $\eta_s(n_2)$ of the following equations $$\cos(2\beta_2+\delta p)=\eta_p(n_2)$$

$$\cos(2\beta_2+\delta s)=\eta_s(n_2)$$

are specified as a function of $n_2$, in accordance with the known values of incident angle $\theta_1$, refractive index of the substrate, refractive index of the incident medium, refractive index and thickness of the thin film layers other than the uppermost layer, and the measured values of reflectances Rp and Rs, wherein $2\beta_2$ is phase change that results from the double traversal of the uppermost thin film, and wherein $\delta_p$ and $\delta_s$ are the phase changes of amplitude reflectances for each of P and S polarized light assuming that the uppermost thin film layer is replaced by an incident medium having the same refractive index as the uppermost thin film. The calculational function specifying step comprises a second sub-step wherein $\xi_p(n_2)$ and $\xi_s(n_2)$ of the following equations $$\tan\delta p=\xi_p(n_2)$$

$$\tan\delta s=\xi_s(n_2)$$

are specified as a function of $n_2$ in accordance with the known values of incident angle $\theta_1$, refractive index of the substrate, and refractive index and thickness of the thin film layers other than the uppermost layer.

In the calculation step, the values of $n_2$, such that it satisfies the following equations, is the correct refractive index of the uppermost layer film and it can be obtained by using a numerical search $$\cos^{-1}\{\eta_p(n_2)\}-\cos^{-1}\{\eta_s(n_2)\}=\tan^{-1}\{\xi_p(n_2)\}-\tan^{-1}\{\xi_s(n_2)\}$$

or $$\cos^{-1}\{\eta_p(n_2)\}-\tan^{-1}\{\xi_p(n_2)\} = \cos^{-1}\{\eta_s(n_2)\}-\tan^{-1}\{\xi_s(n_2)\}$$

The functions $\eta_p(n_2)$, $\eta_s(n_2)$, $\xi_p(n_2)$ and $\xi_s(n_2)$ are determined by using the various optical principles, especially Fresnel equations.

The above mentioned function specifying step and the calculation step are actually carried out by a computer.

Further objects and advantages of the present invention will be apparent from the following description, reference being had to the accompanying drawings wherein preferred embodiments of the present invention are clearly shown.

BRIEF DESCRIPTION OF THE DRAWINGS

The present invention will now be further described with reference to the accompanying drawings wherein.

DETAILED DESCRIPTION OF PREFERRED EMBODIMENTS OF THE PRESENT INVENTION

Figure 1:
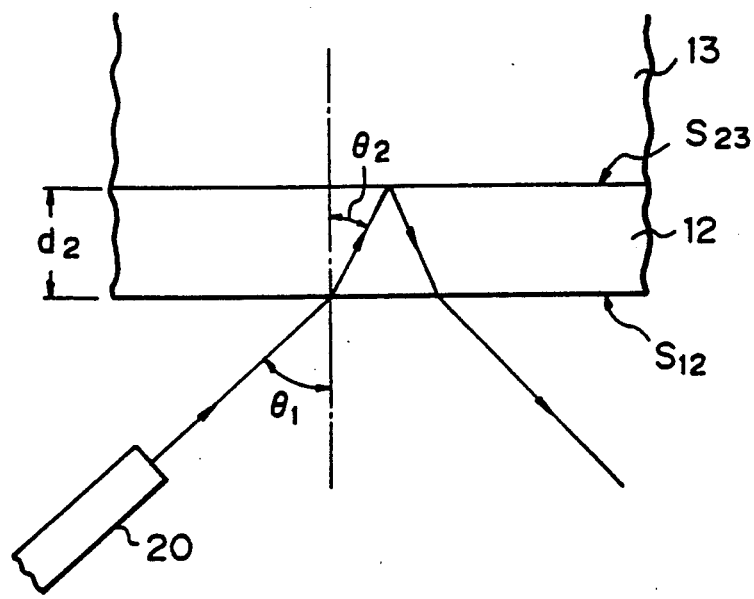
FIG. 1 is an explanatory view for explaining the principle of a first embodiment of the present invention.

First, principle of the first embodiment of the present invention is described with reference to FIG. 1.

In the drawing, reference numeral 13 designates a substrate and 12 designates a thin film, respectively. Also, boundary surface between the thin film 12 and incident medium (air in this particular embodiment) is designated by reference $S_{12}$ and boundary surface between the thin film 12 and the substrate 13 is designated by reference $S_{23}$. The known refractive index $n_3^*$ of the substrate 13 is represented as $n_3^* = n_3(1+ik_3)$. The unknown refractive index of the thin film 12 is represented by $n_2$. The refractive index $n_1$ of the incident medium is represented as $n_1 = 1$, when the incident medium is air.

As illustrated in FIG. 1, a monochromatic light is emitted from a light source 20 toward the thin film 12. The light is multi-reflected in the thin film 12 and emits out of the film. The total amplitude reflectance of the reflected light can be represented, in accordance with Snell laws of refraction and Fresnel equations, as follows.

$$r_{p,s} = \frac{r_{12p,s} + \rho_{23p,s} \exp i(\phi_{23s,p} + 2\beta)}{1 + r_{12p,s} \rho_{23p,s} \exp i(\phi_{23s,p} + 2\beta)} \quad (1)$$

wherein appendant numerals 12 and 23 represent the boundary surface $S_{12}$ or $S_{23}$ on which the light is reflected, and appendant references p and s represent that the incident light is P-polarized light or S-polarized light. Also, $r_{12}$ and $\rho_{23}$ represented in the equation designate amplitude reflectance.

The amplitude reflectance are represented, in accordance with Fresnel equations, as follows.

$$\begin{aligned}
r_{12p} &= \tan(\theta_1 - \theta_2)/\tan(\theta_1 + \theta_2) \\
r_{23s} &= -\sin(\theta_1 - \theta_2)/\sin(\theta_1 + \theta_2) \\
\rho_{23p} &= \tan(\theta_2 - \theta_3^*)/\tan(\theta_2 + \theta_3^*) \\
\rho_{23s} &= -\sin(\theta_2 - \theta_3^*)/\sin(\theta_2 + \theta_3^*)
\end{aligned} \quad (2)$$

wherein the incident angle and refracted angle are represented wherein the incident angle and refracted angle are represented as $\theta_1$ and $\theta_2$, respectively, as shown in FIG. 1, and the complex refraction angle in the substrate is represented as $\theta_3^*$.

For the sake of convenient analysis of the above equations, an assumptive equation $$n_3^* \cos \theta_3^* = u_3 + iv_3$$

is considered, wherein $u_3$ and $v_3$ represent a real number. Then, the following equations are derived from Snell laws of refraction.

$$2u_3^2 = n_3^2(1 - k_3^2) - n_1^2\sin^2\theta_1 + \sqrt{(n_3^2(1 - k_3^2) - n_1^2\sin^2\theta_1)^2 + 4n_3^4k_3^2}$$

$$2v_3^2 = -n_3^2(1 - k_3^2) + n_1^2\sin^2\theta_1 + \sqrt{(n_3^2(1 - k_3^2) - n_1^2\sin^2\theta_1)^2 + 4n_3^4k_3^2}$$

Therefore, $\rho_{23p}$ and $\rho_{23s}$ of the equations (2) can be rewritten as follows:

$$\begin{aligned}
\rho_{23p}^2 &= \frac{(n_3^2(1 - k_3^2)\cos\theta_2 - n_2u_3)^2 + (2n_3^2k_3\cos\theta_2 - n_2v_3)^2}{(n_3^2(1 - k_3^2)\cos\theta_2 + n_2u_3)^2 + (2n_3^2k_3\cos\theta_2 + n_2v_3)^2} \\
\rho_{23s}^2 &= \frac{(n_2\cos\theta_2 - u_3)^2 + v_3^2}{(n_2\cos\theta_2 + u_3)^2 + v_3^2}
\end{aligned} \quad (2)'$$

Also, phase change $\phi_{23p}$, $\phi_{23s}$ of the light reflected on the boundary surface $S_{23}$ is represented as follows.

$$\begin{aligned}
\tan \phi_{23p} &= \frac{2n_2n_3^2\cos\theta_2(2k_3u_3 - (1 - k_3^2)v_3)}{n_3^4(1 + k_3^2)^2\cos^2\theta_2 - n_2^2(u_3^2 + v_3^2)} \\
\tan \phi_{23s} &= \frac{2v_3n_2\cos\theta_2}{u_3^2 + v_3^2 - n_2^2\cos^2\theta_2}
\end{aligned} \quad (3)$$

Also, phase change $2\beta$ that results from the double traversal of the film is represented as follows.

$$2\beta = 4\pi n_2 d_2 (\cos\theta_2)/\lambda \quad (4)$$

wherein $\lambda$ represents wavelength of the light.

The reflectance $R_{p,s}$ is calculated from the equation (1) as follows.

$$R_{p,s} = \frac{r_{12p,s}^2 + \rho_{23p,s}^2 + 2r_{12p,s} \cdot \rho_{23p,s}\cos(\phi_{23p,s} + 2\beta)}{1 + r_{12p,s}^2 \cdot \rho_{23p,s}^2 + 2r_{12p,s} \cdot \rho_{23p,s}\cos(\phi_{23p,s} + 2\beta)} \quad (5)$$

The above equation (5) can be replaced and $\cos(\phi_{23p}+2\beta)$, $\cos(\phi_{23s}+2\beta)$ are given by the following functions $\eta_p$ and $\eta_s$ $$\cos(\phi_{23p} + 2\beta) = \frac{r_{12p}^2 + \rho_{23p}^2 - Rp(1 + r_{12p}^2\rho_{23p}^2)}{2r_{12p}\rho_{23p}(Rp - 1)} \quad (6)$$

$$\equiv \eta_p(n_1,n_2,n_3^*,\theta_1,\lambda,R_p)$$

$$\cos(\phi_{23s} + 2\beta) = \frac{r_{12s}^2 + \rho_{23s}^2 - Rs(1 + r_{12s}^2\rho_{23s}^2)}{2r_{12s}\rho_{23s}(Rs - 1)} \quad (7)$$

$$\equiv \eta_s(n_1,n_2,n_3^*,\theta_1,\lambda,R_s)$$

In the above equations (6) and (7), since the refractive index $n_3*$, $\theta_1$ and $\lambda$ are known ($n_1=1$), if the reflectances $R_p$ and $R_s$ are measured at a certain angle of incident $\theta_1$ (refractive angle is $\theta_2$) representing $\phi_{23p}-\phi_{23s}$, which is the difference between the phase change of the P-polarized light at $S_{23}$ and that of the S-polarized light, by the functions $\eta_p$ and $\eta_s$, we have the following equation $$\cos^{-1}\{\eta_p(n_2)\} - \cos^{-1}\{\eta_s(n_2)\} = \phi_{23p} - \phi_{23s} \quad (8)$$

where unknown parameter is only $n_2$.

Figure 2:
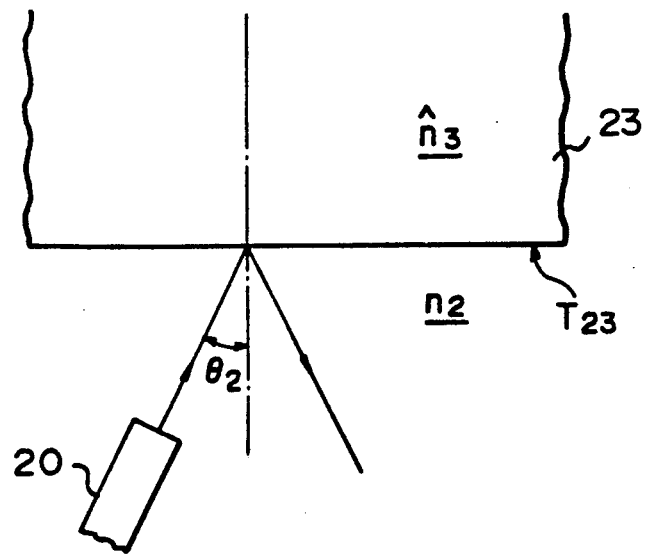
FIG. 2 is another explanatory view for explaining the principle of the first embodiment of the present invention.

Then, with reference to FIG. 2, numeral 23 designates a substrate having the same refractive index $n_3^* = n_3(1+ik_3)$ as the substrate 13 of FIG. 1. The phase change $\phi_{23p}$, $\phi_{23s}$ in the substrate surface $T_{23}$ are represented in the following equations and are defined as the following functions $\xi_p$ and $\xi_s$, wherein each of P-polarized light and S-polarized light is irradiated to the substrate 23 with the incident angle of $\theta_2$ from an ambient medium having the same refractive index $n_2$ as the thin film 12 of FIG. 1.

$$\tan\phi_{23p} = \frac{2n_2n_3^2\cos\theta_2(2k_3u_3 - (1 - k_3^2)v_3)}{n_3^4(1 + k_3^2)^2\cos^2\theta_2 - n_2^2(u_3^2 + v_3^2)} \quad (9)$$

$$\equiv \xi_p(n_1,n_2,n_3^*,\theta_1,\lambda)$$

$$\tan\phi_{23s} = \frac{2V_3n_2\cos\theta_2}{u_3^2 + v_3^2 - n_2^2\cos^2\theta_2} \quad (10)$$

$$\equiv \xi_s(n_1,n_2,n_3^*,\theta_1,\lambda)$$

In the above equations, since $n_1$, $n_3^*$, $\theta_1$ and $\xi$ are known, representing $\phi_{23p}-\phi_{23s}$ by the functions $\xi_p$ and $\xi_s$, we have the following equation $$\tan^{-1}(\xi_p(n_2)) - \tan^{-1}(\xi_s(n_2)) = \phi_{23p} - \phi_{23s} \quad (11)$$

where the only unknown value is $n_2$.

From equations (8) and (11), $$\cos^{-1}\{\eta_p(n_2)\} - \cos^{-1}\{\eta_s(n_2)\} = \tan^{-1}\{\xi_p(n_2)\} - \tan^{-1}\{\xi_s(n_2)\} \quad (12)$$

The value of $n_2$ such that it satisfies equation (12) is the correct value of film index and it can be obtained by using a numerical search.

An actual example of the refractive index measuring method according to the present invention is described hereinafter.

Figure 3:
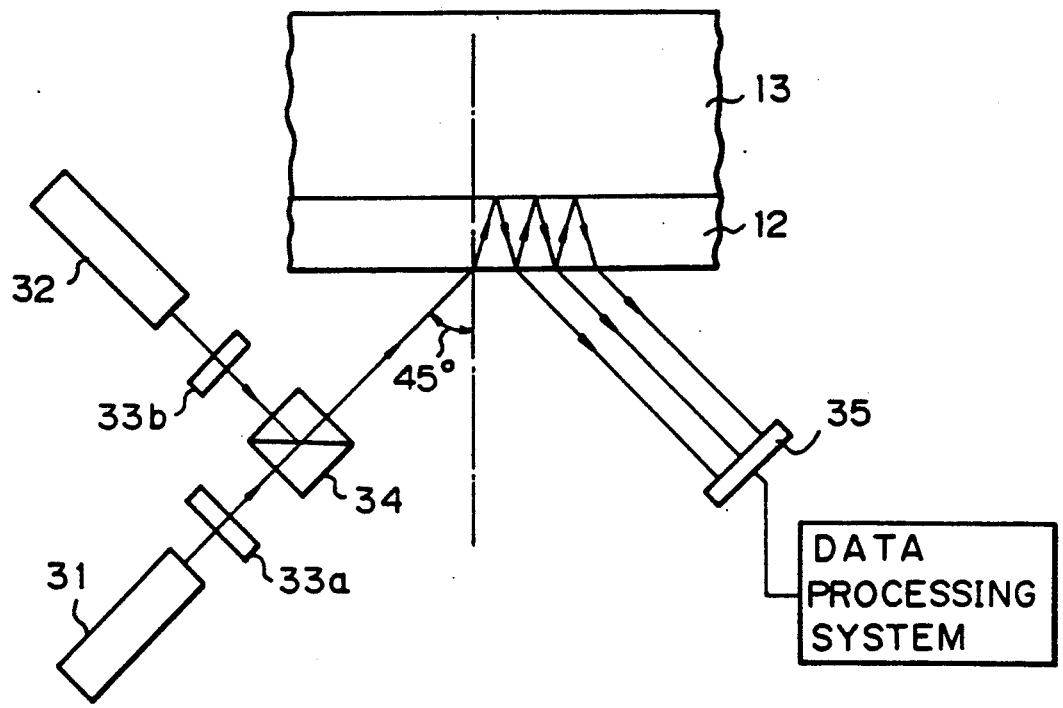
FIG. 3 is a constructional view of an apparatus for carrying out the method according to the present invention.

FIG. 3 illustrates an example of the apparatus for carrying out the measuring method according to the present invention. In the drawing, a substrate 13 having a known refractive index, a thin film 12 to be measured formed on the substrate 13, light sources 31, 32, shutters 33a, 33b each for intervening the light path from each of the light sources, a polarized light beam splitter 34, and a photodetector 35 are illustrated. Each of the light sources 31 and 32 is a He-Ne laser generator which emits a stabilized laser beam of 6328 Å wavelength. The light source 31 is arranged to emit an S-polarized laser and the light source 32 is arranged to emit a P-polarized laser. The shutter 33a is disposed in front of the light source 31 and the shutter 33b is disposed in front of the light source 32 so that the polarization of the incident light can be changed in the reflectance measuring process. Also, the laser from each light source to the thin film 12 is fully monochromized through the beam splitter 34 having a high extinction effect. The angle of incidence to the thin film 12 is usually arranged to be 45 degrees, however, it is not limited to that angle.

In the measuring system illustrated in FIG. 3, the reflectance for each polarized laser can be detected by the photodetector 35 which detects the luminous intensity of the reflected light, changing the light by the shutters 33a and 33b. The data processing system represented in FIG. 3 comprises a well known A-D converter, an interface circuit, a micro-computer and a memory device etc. which constitute an automatic measuring system. The memory device memorizes data processing programs and basic data.

Result of the measurement of the refractive index using some samples is described below. The samples are as follows.

Sample 1

Ag substrate having a large absorption coefficient and $SiO_2$ thin film sputtered thereon;

Sample 2

Si substrate having a low absorption coefficient and $SiO_2$ thin film sputtered thereon;

Sample 3 dielectric Pyrex glass substrate having Courning #7059 glass thin film sputtered thereon.

I. Result from Sample 1

The refractive index $n_3^*$ of the substrate of Ag is 0.065 (1+i·61.53) for the incident light of 6328 Å wavelength. The reflectance is detected by the apparatus of FIG. 3. The measurement results were as follows:
Rs = 0.989426
Rp = 0.979586
Then, $\cos^{-1}(\eta_p(n_2)) - \cos^{-1}\{\eta_s(n_2)\}$ and $\tan^{-1}\{\xi_p(n_2)\} - \tan^{-1}\{\xi_s(n_2)\}$ are calculated in accordance with the above mentioned calculation sequence using the refractive index $n_3^*$ of the Ag substrate and the measured reflectances Rs and Rp and assuming the value of refractive index $n_2$ of the thin film. The calculation result is graphically represented in FIG. 4. The genuine value of the refractive index of the thin film is determined as 1.460 which is a value at the intersection point of the curve of $\cos^{-1}\{\eta_p(n_2)\} - \cos^{-1}\{\eta_s(n_2)\}$ and the curve of $\tan^{-1}\{(\xi_p(n_2)\}\tan^{-1}\{(\xi_s(n_2)\}$ where $\cos^{-1}(\eta_p(n_2)) - \cos^{-1}\{(\eta_s(n_2))\}$ and $\tan^{-1}\{\xi_p(n_2)\} - \tan^{-1}\{\xi_s(n_2)\}$ are equal to each other.

II. Result from Sample 2

The refractive index $n_3^*$ of the substrate of Si is 3.858 $(1+i\cdot 0.00468)$ for the incident light of 6328 Å wavelength. The reflectance is detected by the apparatus of FIG. 3. The measurement results were as follows.

$Rs = 0.154861$
$Rp = 0.128237$

Then, $\cos^{-1}\{\eta_p(n_2)\} - \cos^{-1}\{\eta_s(n_2)\}$ and $\tan^{-1}\{\xi_p(n_2)\} - \tan^{-1}\{\xi_s(n_2)\}$ are calculated in accordance with the above mentioned calculation sequence using the refractive index $n_3^*$ of the Si substrate and the reflectances Rs and Rp and assuming the value of refractive index $n_2$ of the thin film. The calculation result is graphically represented in FIG. 5. The genuine value of the refractive index of the thin film is determined as 1.460 which is the value at the intersection point of the curve of $\cos^{-1}\{\eta_p(n_2)\} - \cos^{-1}\{\eta_s(n_2)\}$ and the curve of $\tan^{-1}\{\xi_p(n_2)\} - \tan^{-1}\{\xi_s(n_2)\}$ where $\cos^{-1}\{\eta_p(n_2)\} - \cos^{-1}\{\eta_s(n_2)\}$ and $\tan^{-1}\{\xi_p(n_2) - \tan^{-1}\{\xi_s(n_2)\}$ are equal to each other

III. Result from Sample 3

The refractive index $n_3^*$ of the substrate of Pyrex glass is 1.472 for the incident light of 6328 Å wavelength. The reflectance is detected by the apparatus of FIG. 3. The measurement results were as follows.

$Rs = 0.098464$
$Rp = 0.009822$

Then, $\cos^{-1}\{(\eta_p(n_2)\} - \cos^{-1}\{\eta_s(n_2)\}$ and $\tan^{-1}\{\xi_p(n_2)\} - \tan^{-1}\{\xi_s(n_2)\}$ are calculated in accordance with the above mentioned calculation sequence using the refractive index $n_3^*$ of the Pyrex glass substrate and the reflectances Rs and Rp and assuming the value of refractive index $n_2$. The calculation result is graphically represented in FIG. 6. The genuine value of the refractive index of the thin film is determined as 1.544 which is the value at the intersection point of the curve of $\cos^{-1}\{\eta_p(n_2)\} - \cos^{-1}\{\eta_s(n_2)\}$ and the curve of $\tan^{-1}\{\xi_p(n_2)\} - \tan^{-1}\{\xi_s(n_2)\}$ where $\cos^{-1}\{\eta_p(n_2)\} - \cos^{-1}\{\eta_s(n_2)\}$ and $\tan^{-1}\{(\xi_p(n_2)\} - \tan^{-1}\{\xi_s(n_2)\}$ are equal to each other.

As can be seen from the above mentioned experimental result, especially from the result of Sample 1 and Sample 2, in accordance with the method for measuring the refractive index of thin film according to the present invention, the same measurement result can be obtained even though the thin film to be measured is disposed on the substrate having a different absorption coefficient.

Therefore, it is possible to accurately measure the refractive index of a thin film formed on a substrate of a high absorptive material, in accordance with the present invention.

Figure 6:
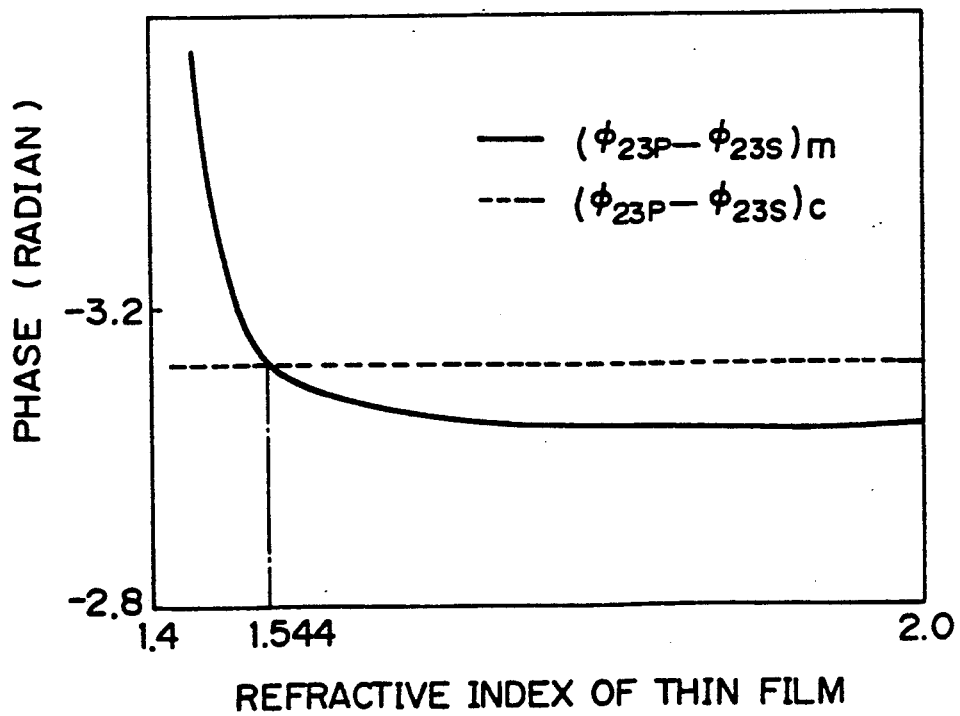
FIG. 6 is still another graphical view showing a result of the measuring method according to the first embodiment of the present invention.
Figure 4:
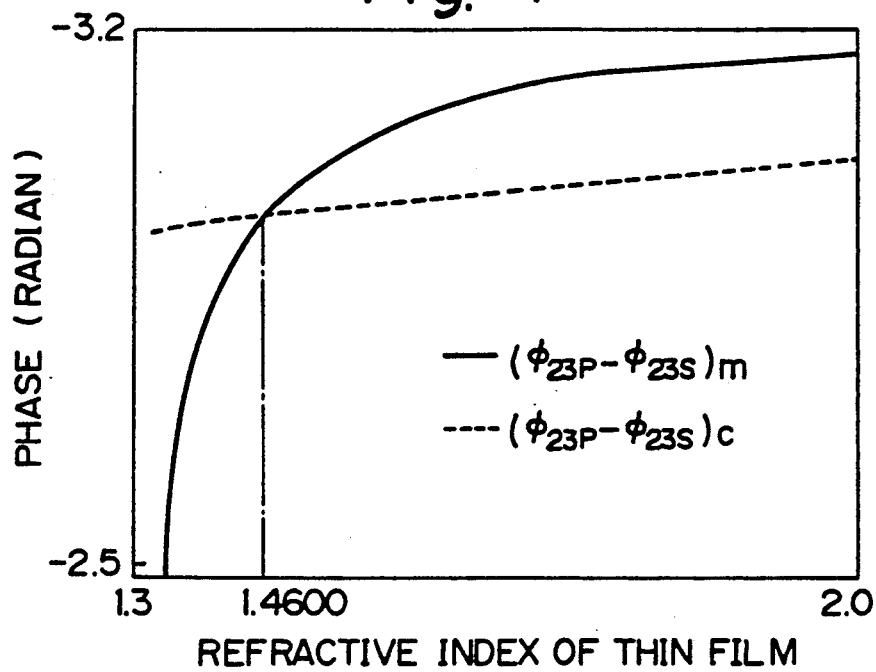
FIG. 4 is a graphical view showing a result of the measuring method according to a first embodiment of the present invention.
Figure 5:
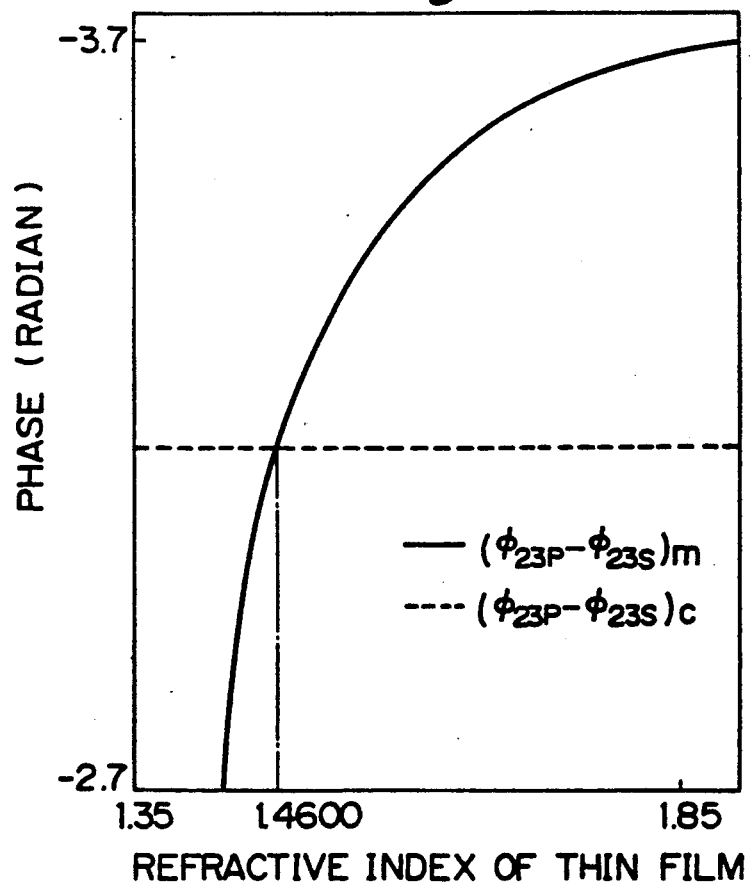
FIG. 5 is another graphical view showing a result of the measuring method according to the first embodiment of the present invention.

Note, although the above mentioned examples of the measurement result are represented by graphs in FIGS. 4 to 6, it is possible to automatically carry out the measurement by using a data processing system assembled with the apparatus of FIG. 3 in cooperation with a microcomputer well known itself. That is, the aforementioned calculation sequence is prememorized in the memory of the microcomputer and the refractive index value of the substrate is input at the beginning of the measurement as an initial input data so that the microcomputer calculates $\cos^{-1}\{\eta_p(n_2)\} - \cos^{-1}\{\eta_s(n_2)\}$ and $\tan^{-1}\{\xi_p(n_2)\} - \tan^{-1}\{Y_s(n_2)\}$ for various assumptive values of refractive index of the thin film in accordance with the predetermined sequence, then determines the calculated values and determines a value as the genuine refractive index when $\cos^{-1}\{\eta_p(n_2)\} - \cos^{-1}\{\eta_s(n_2)\}$ and $\tan^{-1}\{\xi_s(n_2)\}$ are equalized, which value is displayed or recorded, thereby performing an automatic measuring process.

As mentioned above, in accordance with the present invention, the refractive index of a thin film is easily and accurately measured simply by detecting reflectances $R_p$ and $R_s$. Therefore, an apparatus having a simple construction can be used for measuring the refractive index. Also, it is possible to upgrade the accuracy and reliability of measurement of the refractive index, since the measurement result is not influenced by the absorption of the substrate. Further, it is easily possible to arrange an automatic system for measuring the refractive index of a thin film.

Principle of a second embodiment of the present invention is described hereinafter with reference again to FIG. 1 which is also used to explain the aforementioned first embodiment. The preamble portion of the explanation of the first embodiment is also applicable to the second embodiment. Features of the second embodiment compared to the first embodiment are explained hereinafter.

In the second embodiment, the following equations correspond to equations (9) and (10) of the first embodiment.

$$\tan\phi_{23p} = \frac{2n_2n_3^2\cos\theta_2(2k_3u_3 - (1 - k_3^2)v_3)}{n_3^4(1 + k_3^2)^2\cos^2\theta_2 - n_2^2(u_3^2 + v_3^2)} \quad (13)$$

$$\equiv \xi_p(n_1, n_2, n_3^*, \theta_1, \lambda)$$

$$\tan\phi_{23s} = \frac{2V_3n_2\cos\theta_2}{u_3^2 + v_3^2 - n_2^2\cos^2\theta_2} \quad (14)$$

$$\equiv \xi_s(n_1, n_2, n_3^*, \theta_1, \lambda)$$

Also, equations (6) and (7) are replaced by the following equations.

$$\cos(\phi_{23p} + 2\beta) = \eta_p(n_1, n_2, n_3^*, \theta_1, \lambda, R_p) \quad (15)$$

$$\cos(\phi_{23s} + 2\beta) = \eta_s(n_1, n_2, n_3^*, \theta_1, \lambda, R_s) \quad (16)$$

$2\beta$, which is referred to in the explanation of equation (4) of the first embodiment, can be derived from the above equations (13), (15) and equation (5) of the first embodiment and represented as follows.

$$2\beta = \cos^{-1}\{\eta_p(n_1, n_2, n_3^*, \theta_1, \lambda, R_p)\} - \tan^{-1}\{\xi_p(n_1, n_2, n_3^*, \theta_1\lambda)\} \quad (19)$$

$2\beta$ can be also be derived from equations (14), (16) and equation (4) of the first embodiment and represented as follows.

$$2\beta = \cos^{-1}\{\eta_s(n_1, n_2, n_3^*, \theta_1\lambda, R_s)\} - \tan^{-1}\{\xi_s(n_1, n_2, n_3^*, \theta_1\lambda)\} \quad (20)$$

From the above equations (19) and (20), the following equation is derived.

$$\cos^{-1}\{\eta_p(n_1, n_2, n_3^*, \theta_1\lambda, R_p)\} - \tan^{-1}\{\xi_p(n_1, n_2, n_3^*, \theta_1, \lambda)\}$$
$$= \cos^{-1}\{\eta_s(n_1, n_2, n_3^*, \theta_1, \lambda, R_s)\} - \tan^{-1}\{\xi_s(n_1, n_2, n_3^*, \theta_1\lambda)\} \quad (21)$$

A monochromatic light of wavelength $\lambda$ is irradiated to the thin film 12 at an incident angle $\theta_1$ as illustrated in FIG. 1 and reflectance Rp for the P-polarized light and reflectance Rs for the S-polarized light are detected. Each value of $\lambda$, $n_1$, $\theta_1$, $n_3^*$ are known and can be regarded as a constant. Therefore, by substituting these values for the factors in the equation (21) as well as the measured reflectances Rp and Rs, the only unknown factor $n_2$ which is the refractive index of the thin film can be obtained from the equation (21).

The measuring method according to the second embodiment can be carried out with the use of the apparatus of FIG. 3.

Result of the measuring method according to the second embodiment using a sample is as follows.

The sample comprises a silicon (Si) substrate having a thin film of $SiO_2$ formed thereon by heat oxidization. A monochromatic light of wavelength $\lambda$ of 6328 Å is irradiated to the sample at an incident angle 60 degrees and reflectance Rp for the P-polarized light and reflectance Rs for the S-polarized light are detected as follows.

Rp = 0.13611
Rs = 0.18849

Then, $\cos^{-1}\{\eta_p(n_2)\} - \tan^{-1}\{\xi_p(n_2)\}$ and $\cos^{-1}\{\eta_s(n_2)\} - \tan^{-1}\{\xi_s(n_2)\}$ are calculated by substituting the value 3.858 (1+0.00467i) of the refractive index of the Si substrate and the measured values of Rp and Rs for the factors in the equations (19) and (20), varying the assumptive refractive index $n_2$ of the $SiO_2$ film from 1.4 to 1.5. The calculation result is graphically represented in FIG. 7. As can be seen from the graph of FIG. 7, $\cos^{-1}\{\eta_p(n_2)\} - \tan^{-1}\{\xi_p(n_2)\}$ and $\cos^{-1}\{\eta_s(n_2)\} - \tan^{-1}\{\xi_s(n_2)\}$ are equal to each other when $n_2 = 1.460$. Therefore, the refraction index of $SiO_2$ film is determined as 1.460.

As mentioned above, in accordance with the present invention, the refractive index of a thin film formed on a substrate having a known refractive index can be measured by detecting reflectance Rp for the P-polarized light and reflectance Rs for the S-polarized light, which makes it possible to upgrade the accuracy and reliability of measurement with the use of an apparatus having a simple structure.

Figure 7:
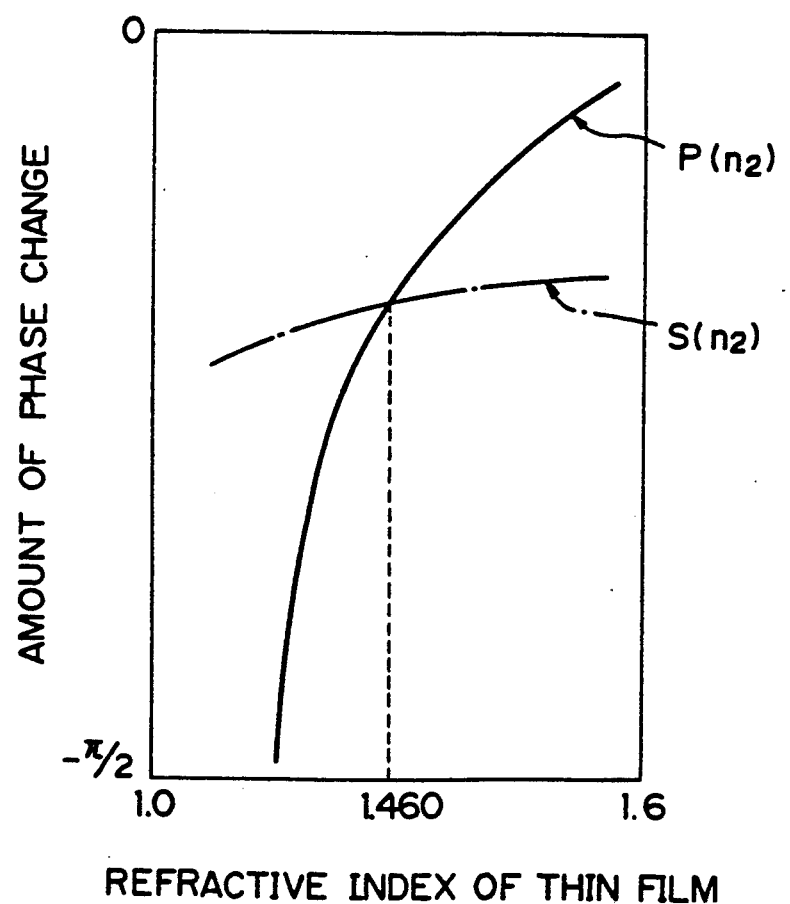
FIG. 7 is a graphical view showing a result of the measuring method according to a second embodiment of the present invention.

Note, although the above mentioned examples of the measurement result are represented by a graph in FIG. 7 wherein the refractive index of the thin film is determined as the value at the intersection point of $\cos^{-1}\{\eta_p(n_2)\} - \tan^{-1}\{\xi_p(n_2)\}$ and $\cos^{-1}\{\eta_s(n_2)\} - \tan^{-1}\{\xi_s(n_2)\}$, it is possible to automatically carry out the measurement by using a data processing system assembled with the apparatus of FIG. 3 in cooperation with a microcomputer well known itself. That is, the aforementioned calculation sequence, wavelength of the light, angle of incidence, etc. are prememorized in the memory of the microcomputer and the refractive index value of the substrate is input at the beginning of the measurement as an initial input data so that the microcomputer calculates $\cos^{-1}\{\eta_p(n_2)\} - \tan^{-1}\{\xi_p(n_2)\}$ and $\cos^{-1}\{\eta_s(n_2)\} - \tan^{-1}\{\xi_s(n_2)\}$ for various assumptive values of refractive index of the thin film in accordance with the predetermined sequence, then compares the calculated values and determines a value as the genuine refractive index when $\cos^{-1}\{\eta_p(n_2)\} - \tan^{-1}\{\xi_p(n_2)\}$ and $\cos^{-1}\{\eta_s(n_2)\} - \tan^{-1}\{\xi_s(n_2)\}$ are equalized, which value is displayed or recorded, thereby performing an automatic measuring process.

As mentioned above, in accordance with the second embodiment of the present invention, as well as the first embodiment, the refractive index of a thin film formed on a substrate having a known refractive index is easily and accurately measured simply by detecting reflectances $R_p$ and $R_s$. Therefore, an apparatus having a simple construction can be used for measuring the refractive index of a thin film formed on a substrate. Also, it is easy to arrange an automatic system for measuring the refractive index of a thin film.

A third embodiment of the present invention will now be described hereinafter with reference to FIGS. 8a and 8b.

Figure 8A:
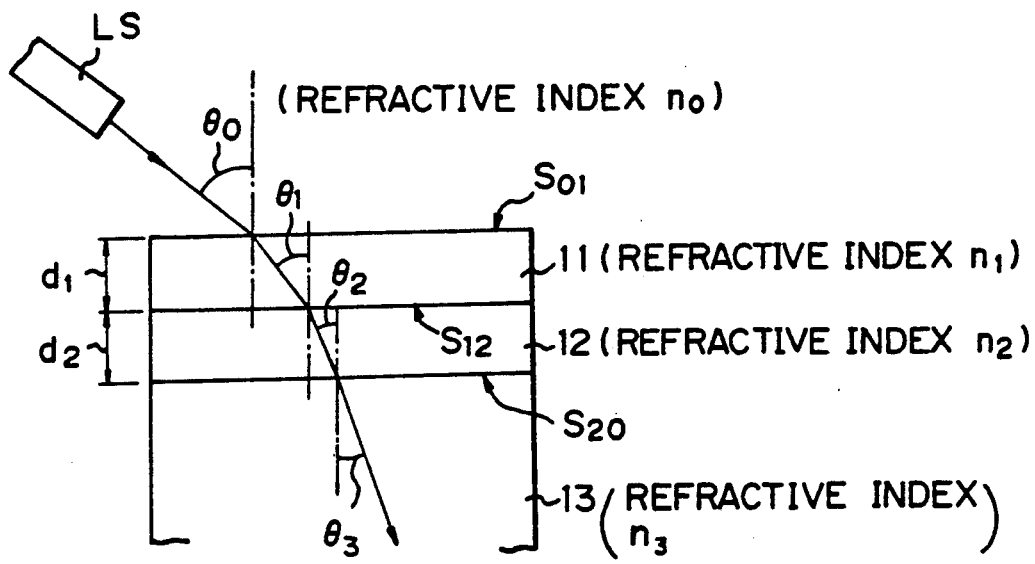
FIGS. 8a and 8b are explanatory views for explaining the principle of a third embodiment of the present invention.
Figure 8B:
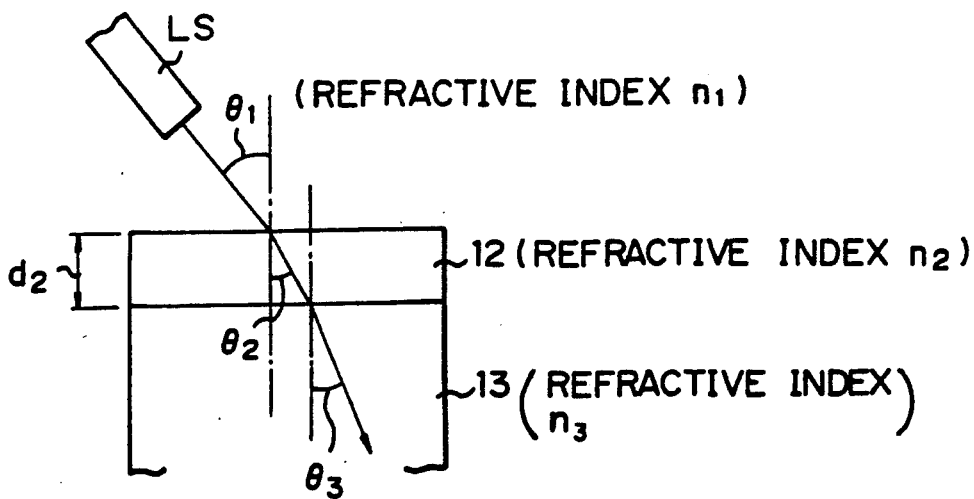

In FIGS. 8a and 8b, reference numeral 13 designates a substrate and reference numerals 11 and 12 designate a thin film, respectively. In FIG. 8a, the refractive index of incident medium is represented by $n_1$. The refractive indices of the thin films are represented by $n_2$ and $n_3$, respectively. Also, the refractive index of the substrate 13 is represented by $n_4$. Also, thickness of the thin films are represented by $d_2$ and $d_3$, respectively. Reference $S_{12}$ designates a boundary surface between the incident medium and the thin film 11. Reference $S_{23}$ designates a boundary surface between the thin films 11 and 12. Also, reference $S_{34}$ designates a boundary surface between the thin film 12 and the substrate 13.

Monochromatic light is irradiated from a monochromatic light source LS to the thin film 11 through the incident medium with an incident angle $\theta_1$. The refraction angles of the light in the thin films 11 and 12 and the substrate 13 are represented by $\theta_2$, $\theta_3$, and $\theta_4$, respectively, as shown in the drawing.

In FIG. 8b, the same thin film 12 as in FIG. 8a is disposed on the same substrate 13 as in FIG. 8a. Monochromatic light emitted from the light source irradiates the thin film 12 through the incident medium which refractive index is $n_2$ with an incident angle $\theta_2$. In FIG. 8b, the same reference as in FIG. 8a represents the same part or means the same thing as in FIG. 8a.

In FIG. 8b, amplitude reflection ratio $r'_{s,p}$ with respect to the monochromatic incident light is represented as follows.

$$r'_{s,p} = [r_{23s,p} + r_{34s,p} \cdot \exp(2i\beta_3)]/[1 + r_{23s,p} \cdot r_{34s,p} \cdot \exp(2i\beta_3)] \quad (31)$$

wherein the appended references S and P represent S-polarized incident light and P-polarized light, respectively, and factors $r_{23s}$, $r_{34s}$, $r_{23p}$, $r_{34p}$ represent Fresnel reflection coefficient on the boundary surfaces $S_{23}$ and $S_{34}$, respectively, and defined by the following equations.

$$r_{23p} = [\tan(\theta_2 - \theta_3)]/[\tan(\theta_2 + \theta_3)]$$

$$r_{23s} = [-\sin(\theta_2 - \theta_3)]/[\sin(\theta_2 + \theta_3 s)]$$

$$r_{34p} = [\tan(\theta_3 - \theta_4)]/[\tan(\theta_3 + \theta_4)]$$

$$r_{34s} = [-\sin(\theta_3 - \theta_4)]/[\sin(\theta_3 + \theta_4)]$$

These factors are rewritten with the use of refractive indices $n_2$, $n_3$ and $n_4$, as follows.

$$r_{23p} = (n_3\cos\theta_2 - n_2\cos\theta_3)/(n_3\cos\theta_2 + n_2\cos\theta_3)$$

$$r_{23s} = (n_2\cos\theta_2 - n_3\cos\theta_3)/(n_2\cos\theta_2 + n_3\cos\theta_3)$$

$$r_{34p} = (n_4\cos\theta_3 - n_3\cos\theta_4)/(n_4\cos\theta_3 + n_3\cos\theta_4)$$

$$r_{34s} = (n_3\cos\theta_3 - n_4\cos\theta_4)/(n_3\cos\theta_3 + n_4\cos\theta_4) \quad (32)$$

Also, $2\beta_3$ represents phase change of the monochromatic light during its propagation from the boundary surface $S_{23}$ to the other boundary surface $S_{34}$ and can be represented with the use of the wavelength $\lambda$ of the monochromatic light by the following equation.

$$2\beta_3 = 4\pi n_3 d_3 (\cos\theta_3)/\lambda \tag{33}$$

On the other hand, with respect to the amplitude reflectance $r_{s,p}$ for the monochromatic incident light, since the amplitude reflectance is equal to $r'_{s,p}$ of equation (31), the amplitude reflectance $r_{s,p}$ can be represented by the following equation.

$$r_{s,p} = [r_{12s,p} + r'_{s,p}\cdot\exp(2i\beta_2)]/[1 + r_{12s,p}\cdot r'_{s,p}\cdot\exp(2i\beta_2)] \tag{34}$$

where $r_{12s,p}$ is Fresnel reflection coefficient on the boundary surface $S_{12}$, and defined by the following equations.

$$r_{12p} = [\tan(\theta_1 - \theta_2)]/[\tan(\theta_1 + \theta_2)]$$

$$r_{12s} = [-\sin(\theta_1 - \theta_2)]/[\sin(\theta_1 + \theta_2)]$$

which can be rewritten with the use of refractive indices $n_1$ and $n_2$ by the following equations.

$$r_{12p} = (n_2\cos\theta_1 - n_1\cos\theta_2)/(n_2\cos\theta_1 + n_1\cos\theta_2)$$

$$r_{12s} = (n_1\cos\theta_1 - n_2\cos\theta_2)/(n_1\cos\theta_1 + n_2\cos\theta_2) \tag{35}$$

Also, $2\beta_2$ represents phase change of the monochromatic light during its propagation from the boundary surface $S_{12}$ to the other boundary surface $S_{23}$ and can be represented with the use of the wavelength $\lambda$ of the monochromatic light, similarly to the aforementioned equation (33), by the following equation.

$$2\beta_2 = 4\pi n_2 d_2 (\cos\theta_2)/\theta \tag{36}$$

The explanation mentioned above refers to the arrangement wherein two layers of thin film 11 and 12 are disposed on the substrate 13. However, the present invention can be applied to the arrangement wherein three or more layers of thin film are disposed on the substrate, by repeating the above mentioned steps. Consequently, when a plurality of thin film layers are formed on a substrate as a multi-layered film, the amplitude reflectance $r_{s,p}$ of monochromatic light irradiated to the multi-layered film through the incident medium having a refractive index of $n_1$ is determined as the amplitude reflectance $r'_{s,p}$ of the monochromatic light irradiated to the multi-layered film in which the uppermost thin film is assumed to be removed through the incident medium having a refractive index of $n_2$, derived from equation (34) wherein $r_{12s,p}$ is the amplitude reflectance on the boundary surface between the incident medium and the uppermost thin film (refractive index $n_2$, film thickness $d_2$).

Also, the reflectance $R_{s,p}$ in this case is represented by the following equation.

$$\begin{aligned} R_{s,p} &= |r_{s,p}|^2 \\ &= r^2_{12s,p} + r'^2_{s,p} + r_{12s,p}\cdot r'_{s,p}\cos2\beta_2)/ \\ &\quad (1 + r^2_{12,sp}\cdot r'^2_{s,p} + 2r_{12s,p}\cdot r'_{s,p}\cos2\beta_2) \end{aligned} \tag{37}$$

This equation (37) can be solved with respect to $\cos2\beta_2$ for each S and P-polarized light, the calculation result being as follows.

$$\cos2\beta_2 = [r^2_{12s} + r'^2_s - R_s(1 + r^2_{12s}\cdot r'^2_s)]/2r_{12s}\cdot r'_s(R_s - 1) \tag{38}$$

$$\cos2\beta_2 = [r^2_{12p} + r'^2_p - R_p(1 + r^2_{12p}\cdot r'^2_p)]/2r_{12p}\cdot r'_p(R_p - 1) \tag{39}$$

Now, a multi-layered thin film having a layer number m which is more than one is considered hereinafter. The refractive index of the substrate is represented by $n_s$. The refractive indices of the thin films are represented $n_2, n_3, \ldots n_m$ in order from the uppermost layer. Also, the thickness of the thin films are represented by $d_2, d_3, \ldots d_m$ in order from the uppermost layer. The refractive index and thickness of the uppermost layer are $n_2$ and $d_2$, respectively.

When the refractive indices other than that of the uppermost thin film and the film thicknesses other than that of the uppermost thin film are known, a monochromatic light having a wavelength $\lambda$ is irradiated to this multi-layered film disposed in an incident medium having a refractive index $n_1$ and reflectance for each S and P-polarized light is detected. The measured value of the reflectance $R_s$ and the known values of $\theta_1, n_s, n_3$ to $n_m$ and $d_3$ to $d_m$ are substituted for the corresponding factors in equation (38) so as to calculate the right side of this equation to represent the calculated result by $S(n_2)$ which is a function of the only unknown factor $n_2$. Also, the measured value of the reflectance $R_p$ and the known values of $\theta_1, \lambda, n_s, n_3$ to $n_m$ and $d_3$ to $d_m$ are substituted for the corresponding factors in equation to represent the calculated result by $P(n_2)$ which is also a function of the only unknown factor $n_2$. $S(n_2)$ and $P(n_2)$ derived from equations (38) and (39) are represented by the following equations.

$$S(n_2) = [r^2_{12s} + r'^2_s - R_s(1 + r^2_{12s}\cdot r'^2_s)]/2r_{12s}\cdot r'_s(R_s - 1) \tag{40}$$

$$P(n_2) = [r^2_{12p} + r'^2_p - R_p(1 + r^2_{12p}\cdot r'^2_p)]/2r_{12p}\cdot r'_p(R_p - 1) \tag{41}$$

To summarize the above calculations, phase change $\beta_2$ of the monochromatic light during its propagation from the boundary surface $S_{12}$ between the incident medium and the uppermost film to the boundary surface $S_{23}$ between the uppermost film and the film next to the uppermost film is specified by the functions $S(n_2)$ and $P(n_2)$ with respect to the unknown factor $n_2$. The functions $S(n_2)$ and $P(n_2)$ varies individually according as the variable $n_2$ changes. When the value of $n_2$ coincides with the genuine refractive index of the uppermost thin film, the following equation is satisfied.

$$S(n_2) = P(n_2)$$

Therefore, the genuine refractive index of the uppermost thin film can be determined as the value of $n_2$ which satisfies the equation $S(n_2) = P(n_2)$, by calculating each function $S(n_2)$, $P(n_2)$ changing the value of parameter $n_2$, then comparing the calculated $S(n_2)$ and $P(n_2)$. Such a calculation can be carried out by a computer. The computer cannot continuously change the parameter $n_2$ but changes the parameter stepwise. Therefore, it is not possible to strictly solve the equation $S(n_2) = P(n_2)$. However, it is possible to specify the value of the refractive index $n_2$ with a required accuracy by a minute step change of the parameter.

Experimental results of the measurement according to this embodiment of the present invention will be explained below.

Sample 1

A measured sample comprises a $SiO_2$ substrate of refractive index 1.460 having a SiN film of refractive index 2.000 and thickness of 5000 Å coated thereon by plasma CVD process, and then forming a Corning #7059 glass thereon by sputtering process.

Figure 9:
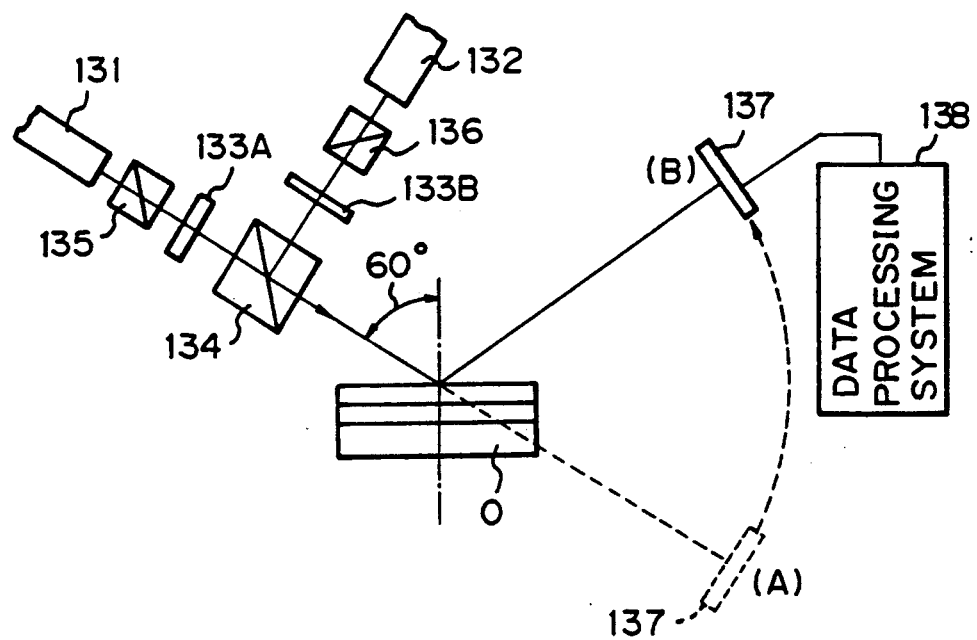
FIG. 9 is a constructional view of an apparatus for carrying out the method in accordance with the third embodiment of the present invention.

The sample is measured with the use of an apparatus illustrated in FIG. 9.

In FIG. 9, reference numerals 131,132 designate an He-Ne laser source which emits a stabilized laser beam of wavelength 6328 Å. A glan-Thomsom prism 135,136 is disposed in front of each of the light sources 131 and 132 so as to obtain an S-polarized light and a P-polarized light from the light sources. The S and P-polarized light can be selected by changing shutters 133A and 133B so as to selectively irradiate the sample 0 to be measured through a polarization beam splitter 134 having a high extinction ratio.

The angle of incidence of the light to the sample is arranged to be 60 degrees in the drawing. However, the angle of incidence is not limited to that angle.

First, a photodetector 137 is disposed at a position (A) depicted by a dashed line without placing the sample 0 at a measuring position on the light path between the light source and the detector 137 so as to directly detect the luminous intensity of the polarized light which directly irradiates the photodetector. Firstly, the S-polarized laser light is directly detected by opening the shutter 133A and closing the shutter 133B. Then, the photodetector 137 is moved to a position (B) depicted by a solid line and the sample 0 is placed on the measuring position as illustrated in the drawing. With this arrangement, the reflectance $R_s$ for the S-polarized laser light which is reflected by the sample 0 and directed to the photodetector 137 is measured. Secondly, the reflectance $R_p$ for the P-polarized laser light is measured in accordance with the same process as for the S-polarized laser mentioned above.

The result of the measurement is as follows.

$R_s$ (60 degrees) = 0.12621
$R_p$ (60 degrees) = 0.01313

The data processing system 38 processes calculation to determine the refractive index using the result of the measurement in accordance with the following sequence.

First, phase change amount of each P and S-polarized light is specified as a function of the refractive index $n_2$ in a manner described below.

The equations (32) and (35) are rewritten in accordance with Snell laws of refraction, when $n_1 = 1$, as follows.

$$r_{12p} = (\sqrt{n_2^2 - \sin^2\theta_1} - \sqrt{1 - \sin^2\theta_1})(\sqrt{n_2^2 - \sin^2\theta_1} \cdot \sqrt{1 - \sin^2\theta_1} - \sin^2\theta_1)/(\sqrt{n_2^2 - \sin^2\theta_1} + \sqrt{1 - \sin^2\theta_1})(\sqrt{n_2^2 - \sin^2\theta_1} \cdot \sqrt{1 - \sin^2\theta_1} + \sin^2\theta_1)$$

$$r_{12s} = (\sqrt{1 - \sin^2\theta_1} - \sqrt{n_2^2 - \sin^2\theta_1})/(\sqrt{1 - \sin^2\theta_1} + \sqrt{n_2^2 - \sin^2\theta_1})$$

$$r_{23p} = (\sqrt{n_3^2 - \sin^2\theta_1} - \sqrt{n_2^2 - \sin^2\theta_1})/(\sqrt{n_3^2 - \sin^2\theta_1} \cdot \sqrt{n_2^2 - \sin^2\theta_1} - \sin^2\theta_1)/(\sqrt{n_3^2 - \sin^2\theta_1} + \sqrt{n_2^2 - \sin^2\theta_1}) \cdot (\sqrt{n_3^2 - \sin^2\theta_1} \cdot \sqrt{n_2^2 - \sin^2\theta_1} + \sin^2\theta_1)$$

$$r_{23s} = (\sqrt{n_2^2 - \sin^2\theta_1} - \sqrt{n_3^2 - \sin^2\theta_1})/(\sqrt{n_2^2 - \sin^2\theta_1} + \sqrt{n_3^2 - \sin^2\theta_1})$$

$$r_{34p} = (\sqrt{n_4^2 - \sin^2\theta_1} - \sqrt{n_3^2 - \sin^2\theta_1})(\sqrt{n_4^2 - \sin^2\theta_1} \cdot \sqrt{n_3^2 - \sin^2\theta_1} - \sin^2\theta_1)/(\sqrt{n_4^2 - \sin^2\theta_1} + \sqrt{n_3^2 - \sin^2\theta_1})(\sqrt{n_4^2 - \sin^2\theta_1} \cdot \sqrt{n_3^2 - \sin^2\theta_1} + \sin^2\theta_1)$$

$$r_{34s} = (\sqrt{n_3^2 - \sin^2\theta_1} - \sqrt{n_4^2 - \sin^2\theta_1})/(\sqrt{n_3^2 - \sin^2\theta_1} + \sqrt{n_4^2 - \sin^2\theta_1})$$

Substituting the values of Rp(60), Rs(60), the incident angle $\theta_1 = 60$ degrees, the wavelength $\lambda = 6328$ Å, the refractive index $n_s = 1.460$ of substrate, the refractive index $n_3 = 2.000$ of SiN film, and the film thickness $d_3 = 5000$ Å into the right sides of equations (40) and (41), then the functions $S(n_2)$ and $P(n_2)$ are calculated by assuming the refractive index $n_2$ of Corning #7059 glass by step of every 0.001 (this step amount is not restricted to be 0.001) within a range of 1.5 to 1.6 (these lower and upper limits of the range could be arbitrarily varied depending on the measurement object).

Figure 11:
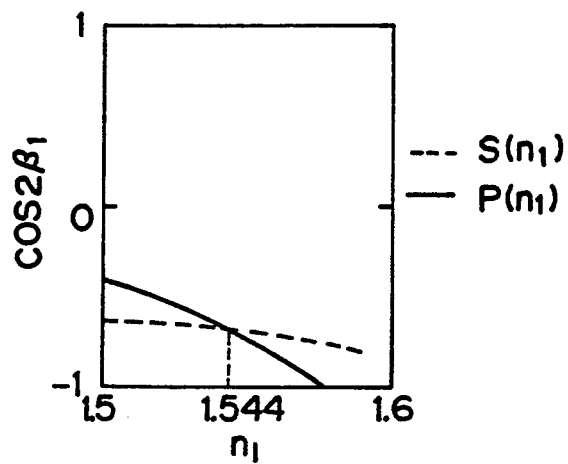
FIG. 11 is a graphical view showing a result of the measuring method carried out by the apparatus of FIG. 9.

The variations of $P(n_2)$ and $S(n_2)$ in response with differing the values of $n_2$ are represented in FIG. 11. As can be seen from FIG. 11, the equations $P(n_2) = S(n_2)$ is satisfied by assuming $n_2 = 1.544$. Therefore the value of 1.544 for $n_2$ can be determined as the refractive index of Corning #7059 glass film.

Sample 2

A measured sample comprises a Pyrex substrate of refractive index 1.472 having a film of Corning #7059 glass of refractive index 1.544 with thickness 5000 Å thereon by sputtering process, and then forming a SiN film thereon by plasma CVD process.

Figure 10:
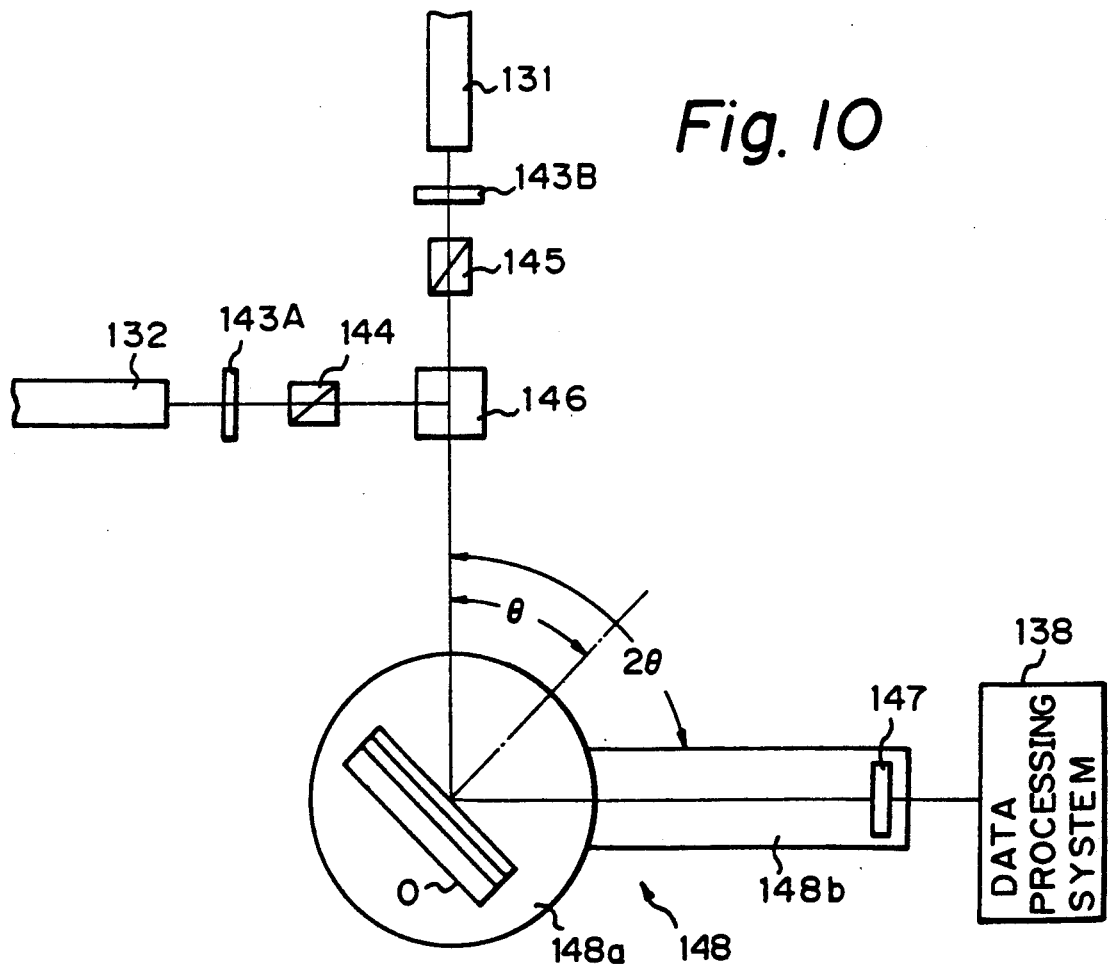
FIG. 10 is a constructional view of another example of the apparatus for carrying out the method according to the third embodiment of the present invention.

The sample is measured with the use of an apparatus illustrated in FIG. 10.

In FIG. 10, reference numerals 131,132 designate an He-Ne laser source which emits a stabilized laser beam of wavelength 6328 Å, as in the apparatus of sample 1. A polarizer 144,145 is disposed in front of each of the light sources 131 and 132 so as to obtain an S-polarized light and a P-polarized light from the light sources. The S and P-polarized light can be selected by changing shutters 143A and 143B so as to selectively irradiate the sample 0 to be measured through a polarization beam splitter 146 having a high extinction ratio.

The sample 0 and a photodetector 147 are disposed on a table 148a and an arm 148b of a $\theta - 2\theta$ rotation system 148, respectively, as illustrated in the drawing. The $\theta - 2\theta$ rotation system 148 functions in a manner that when the table 148a on which the sample 0 is placed rotates by an angle $\theta$, the arm 148b which supports the photodetector 147 rotates by an angle $2\theta$ in the same direction as the table, thereby the photodetector 147 can detect the light reflected by the sample 0 at any rotation angle from zero to 90 degrees.

First, the S-polarized laser light is directly irradiated to and detected by the photodetector 147 by not placing the sample 0 on the table. After that, the sample 0 is placed on the table and the reflectance for the S-polarized light is measured with respect to incident angles 45 and 60 degrees. Then, the reflectance for the P-polarized light is measured in the similar manner.

The result of the measurement is as follows.

$R_s$ (45 degrees) = 0.09395
$R_s$ (60 degrees) = 0.25525
$R_p$ (45 degrees) = 0.00915
$R_p$ (60 degrees) = 0.00636

For the incident angles 45 and 60 degrees, the refractive indices $n_2$ of SiN film for each angle are calculated by the same manner as described in the Sample 1. (assuming the range of $n_2$ is 1.800 to 2.200 with the step amount of 0.001)

Figure 12A:
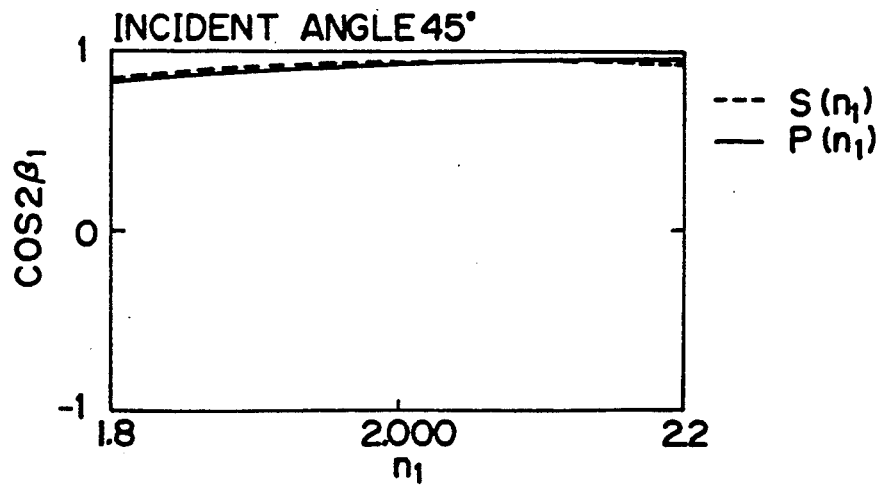
FIGS. 12a and 12b are graphical views showing a result of the measuring method carried out by the apparatus of FIG. 10.

The results of $P(n_2)$ and $S(n_2)$ for the incident angle 45 degrees are shown in FIG. 12(a).

Figure 12B:
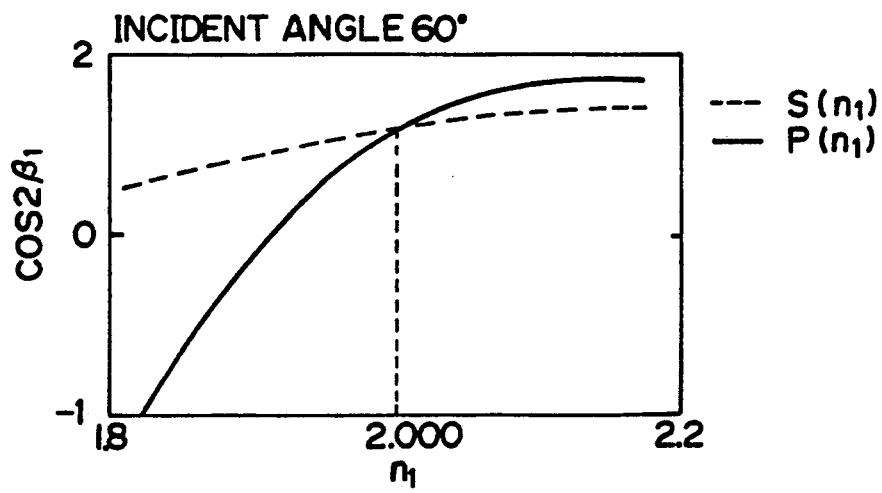

The results of $P(n_2)$ and $S(n_2)$ for the incident angle 60 degrees are shown in FIG. 12(b).

The refractive index $n_2 = 2.000$ for FIG. 12(b), i.e., for the incident angle 60 degrees can be determined since the functions $P(n_2)$ and $S(n_2)$ intersect very clearly, but for FIG. 12(a), i.e., for the incident angle 45 degrees, it is difficult to determine the intersection point of the functions $P(n_2)$ and $S(n_2)$ because the graphs of $P(n_2)$ and $S(n_2)$ are too similar.

When it is measuring with various incident angles, the refractive index $n_2$, derived from the data for the incident angle at where the graphs of $P(n_2)$ and $S(n_2)$ intersect clearly, has more high precision. For this case, the value of 2.000 derived from the data for the incident angle 60 degrees is selected as the desired refractive index of SiN film. The incident angles at where the graphs of $P(n_2)$ and $S(n_2)$ intersect clearly are differed depending on the film of the measurement object.

Principle of a fourth embodiment of the present invention will now be described hereinafter with reference to FIG. 13a and 13b.

Figure 13A:
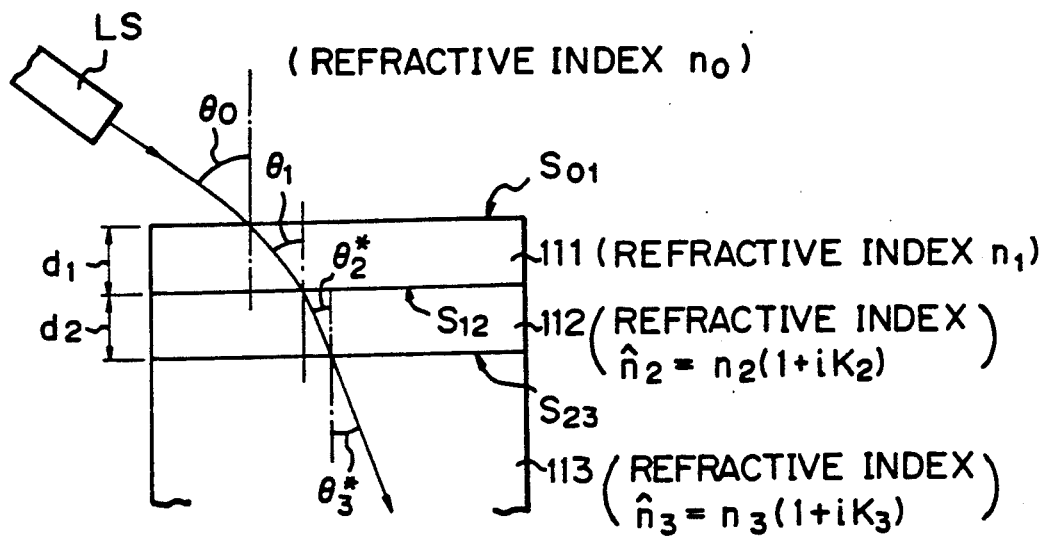
FIGS. 13a and 13b are explanatory views for explaining the principle of a fourth embodiment of the present invention.

In FIG. 13a, thin films and 112 are stacked on a substrate 113. The uppermost thin film 111. is the questioned thin film to be measured, $S_{12}$ designates a boundary surface between the incident medium and the thin film 111. $S_{23}$ designates a boundary surface between the thin films 111 and 112. Also, $S_{34}$ designates a boundary surface between the thin film 112 and the substrate 113. The refractive indices of the incident medium, the thin film 111, the thin film 112 and the substrate 113 are represented by $n_1$, $n_2$, $n_3 = n_3(1 + k_3)$, $n_4 = n_4(1 + ik_4)$, respectively. Thickness of the thin films 111 and 112 are represented by $d_2$ and $d_3$, respectively, as illustrated in the drawing. The angle of incidence of the laser light irradiated to the thin film 111 is represented by $\theta_1$. The refraction angle on each of the boundary surfaces $S_{12}$, $S_{23}$ and $S_{34}$ is represented by $\theta_2$, $\theta_3^*$ and $\theta_4^*$, respectively.

The values of $n_1$, $n_3$, $n_4$ and $d_3$ are known. Also, the incident angle $\theta_1$ and the wavelength $\lambda$ of the incident light from the laser light source LS can be determined as a measurement condition factor.

Figure 13B:
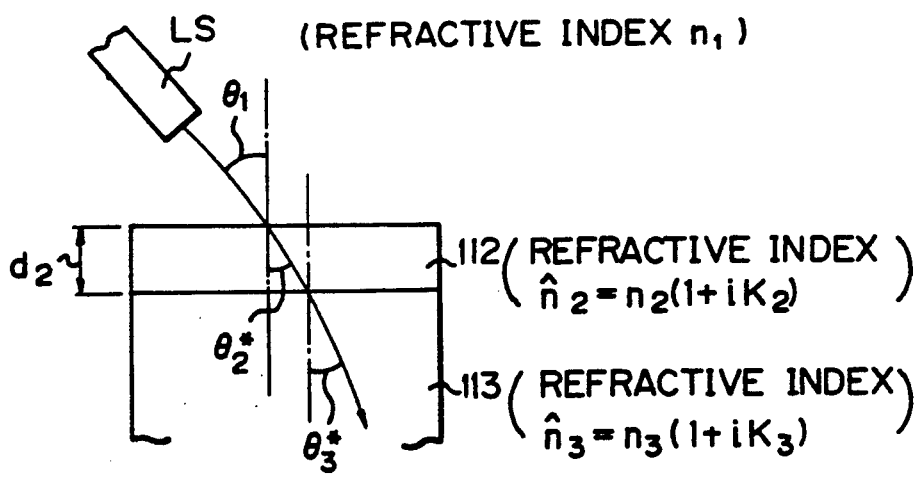

FIG. 13b represents a state wherein an incident light propagates through the incident medium of refractive index $n_2$ to the thin film 112 formed on the substrate 113 from the direction of incident angle $\theta_2$.

When the monochromatic light emitted from the laser source LS is irradiated to the thin film as an incident light as illustrated in FIG. 13b, the amplitude reflectance is represented by the following equation.

$$r'_{s,p} = [r_{23s,p} + r_{34s,p}\exp(2i\beta_3^*)]/[1 + r_{23s,p}r_{34s,p}\exp(2i\beta_3^*)] \quad (51)$$

in which the appended references S and P represent whether the incident light is S-polarized light or P-polarized light and $r_{23}$, $r_{34}$ each represents the Fresnel reflection coefficient on the boundary surface $S_{23}$, $S_{34}$. The above Fresnel reflection coefficients can be represented with the use of the incident angle $\theta_2$ and the refraction angles $\theta_3^*$ and $\theta_4^*$, as follows.

$$r_{23p} = \tan(\theta_2 - \theta_3^*)/\tan(\theta_2 + \theta_3^*) \quad (52\text{-}1)$$

$$r_{23s} = -\sin(\theta_2 - \theta_3^*)/\sin(\theta_2 + \theta_3^*) \quad (52\text{-}2)$$

$$r_{34p} = \tan(\theta_3^* - \theta_4^*)/\tan(\theta_3^* + \theta_4^*) \quad (52\text{-}3)$$

$$r_{34s} = -\sin(\theta_3^* - \theta_4^*)/\sin(\theta_3^* + \theta_4^*) \quad (52\text{-}4)$$

Also, $2\beta_3^*$ represented in the equation (51) designates phase change of the light during its propagation from the boundary surface $S_{23}$ to the boundary surface $S_{34}$ and can be rewritten as follows.

$$2\beta_3^* = 4\pi n_3 d_3 (\cos\theta_3^*)/\lambda \quad (53)$$

Again, with reference to FIG. 13a, the amplitude reflectance $r_{s,p}$ of the two-layered thin film comprising thin film layers 111 and 112 can be represented by the following equation, since the amplitude reflectance on the boundary surface $S_{23}$ is equal to $r'_{s,p}$ represented in the above equation (51).

$$r_{s,p} = [r_{12s,p} + r'_{s,p}\exp(2i\beta_2)]/[1 + r_{12s,p}r'_{s,p}\exp(2i\beta_2)] \quad (54)$$

wherein $r_{12}$ is Fresnel reflection coefficient on the boundary surface $S_{12}$ and represented by the following equations.

$$r_{12p} = \tan(\theta_1 - \theta_2)/\tan(\theta_1 + \theta_2) \quad (55\text{-}1)$$

$$r_{12s} = \sin(\theta_1 - \theta_2)/\sin(\theta_1 + \theta_2) \quad (55\text{-}2)$$

Also, $2\beta_2$ is represented as follows.

$$2\beta_2 = 4\pi n_2 d_2(\cos\theta_2)/\lambda \quad (56)$$

When further thin films are disposed on the substrate 113 (between the substrate and the lower thin film 112), the total amplitude reflectance $r_{s,p}$ of a multi-layered thin film formed on a substrate can be given by the above equation (54), where $r'_{s,p}$ is the amplitude reflectance when the light is incident at the underlying film except the uppermost layer film from the incident medium which has the same refractive index as the uppermost layer film.

Generally, $r'_{s,p}$ is a complex number and is defined as $$r'_{s,p} = \rho'_{s,p} \exp(\delta_{s,p}) \qquad (5)$$

then the equation (54) is rewritten as $$r_{s,p} = [r_{12s,p} + \rho'_{s,p}\exp\{i(2\beta_2 + \delta_{s,p})\}]/[1 + r_{12s,p}\rho'_{s,p}\exp\{i(2\beta_2 + \delta_{s,p})\}]$$

therefore, the reflectance is represented by the following equations.

$$R_p = |r_p|^2 = [r_{12p}^2 + \rho'_p{}^2 + 2r_{12p}\rho'_p\cos(2\beta_2 + \delta_p)]/ \qquad (57)$$
$$[1 + r_{12p}^2\rho'_p{}^2 + 2r_{12p}\rho'_p\cos(2\beta_2 + \delta_p)]$$

$$R_s = |r_s|^2 = [r_{12s}^2 + \rho'_s{}^2 + 2r_{12s}\rho'_s\cos(2\beta_2 + \delta_s)]/ \qquad (58)$$
$$[1 + r_{12s}^2\rho'_s{}^2 + 2r_{12s}\rho'_s\cos(2\beta_2 + \delta_s)]$$

The above equations can be replaced, and $\cos(2\beta_2+\delta_p)$ and $\cos(2\beta_2+\delta_s)$ are given by the following functions $\eta_p$ and $\eta_s$ $$\cos(2\delta_2+\delta_p) = [r_{12p}^2+\rho'_p{}^2-R_p(1+r_{12p}^2\rho'_p{}^2)]/$$
$$[2r_{12p}\rho'_p(R_p-1)] = \rho_p(n_1,n_2,n_3,k_3,n_4,k_4,d_2,\theta_1,\rho,R_p) \qquad (59)$$

$$\cos(2\beta_2+\delta_s) = [r_{12s}^2+\rho'_s{}^2-R_s(1+r_{12s}^2\rho'_s{}^2)]/$$
$$[2r_{12s}\eta'_s(R_s-1)] = \eta_s(n_1,n_2,n_3,k_3,n_4,k_4,d_2,\theta_1,\lambda,R_s) \qquad (60)$$

On the other hand, $\delta_s$, $\delta_p$, $\rho_p$ and $\rho'_s$ can be represented as a function of the refractive index $n_2$ of the uppermost thin film under the condition wherein the refractive index of the substrate and the refractive indices and thickness of the thin film layers other than the uppermost thin film are known in which the absorption coefficient is considered. With regard to the two layered thin film as illustrated in FIG. 13a, the above factors $\delta_s$, $\delta_p$, $\rho'_p$ and $\rho'_s$ can be represented by the following equations.

And $\tan \delta_p$ and $\tan \delta_s$ are defined as the following functions $\xi_p$ and $\xi_s$ $$\tan \delta_p = [\rho_{34p}(1 - \rho_{23p}^2)\sin(u_3\alpha + \phi_{34p}) + \qquad (61)$$
$$\rho_{23p}(\exp\{v_3\alpha\} - \rho_{34p}^2\exp\{-v_3\alpha\})\sin\phi_{23p}]/$$
$$[\rho_{34p}(1 + \rho_{23p}^2)\cos(u_3\alpha + \phi_{34p}) +$$
$$\rho_{23p}(\exp\{v_3\alpha\} + \rho_{34p}^2\exp\{-v_3\alpha\})\cos\phi_{23p}] =$$
$$\xi_p(n_1, n_2, n_3, k_3, n_4, k_4, d_3, \theta_1, \lambda)$$

$$\tan \delta_s = [\rho_{34s}(1 - \rho_{23s}^2)\sin(u_3\alpha + \phi_{34s}) + \qquad (62)$$
$$\rho_{23s}(\exp\{v_3\alpha\} - \rho_{34s}^2\exp\{-v_3\alpha\})\sin\phi_{23s}]/$$
$$[\rho_{34s}(1 + \rho_{23s}^2)\cos(u_3\alpha + \phi_{34s}) +$$
$$\rho_{23s}(\exp\{v_3\alpha\} + \rho_{34s}^2\exp\{-v_3\alpha\})\cos\phi_{23s}] =$$
$$\xi_s(n_1, n_2, n_3, k_3, n_4, k_4, d_3, \theta_1, \lambda)$$

$$|\rho'_p|^2 = [\rho_{23p}^2\exp\{v_3\alpha\} + \rho_{34p}^2\exp\{-v_3\alpha\} + \qquad (63)$$
$$2\rho_{23p}\rho_{34p}\cos(\phi_{34p} - \phi_{23p} + u_3\alpha)]/$$
$$[\exp\{v_3\alpha\} + \rho_{23p}^2\rho_{34p}^2\exp\{-v_3\alpha\} +$$
$$2\rho_{23p}\rho_{34p}\cos(\phi_{23p} + \phi_{34p} + u_3\alpha)]$$

$$|\rho'_s|^2 = [\rho_{23s}^2\exp\{v_3\alpha\} + \rho_{34s}^2\exp\{-v_3\alpha\} + \qquad (64)$$
$$2\rho_{23s}\rho_{34s}\cos(\phi_{34s} - \phi_{23s} + u_3\alpha)]/$$
$$[\exp\{v_3\alpha\} + \rho_{23s}^2\rho_{34s}^2\exp\{-v_3\alpha\} +$$
$$2\rho_{23s}\rho_{34s}\cos(\phi_{23s} + \phi_{34s} + u_3\alpha)]$$

wherein substitutions are made as follows.

$$n_3^*\cos\theta_3^* = u_3 + iv_3, \quad n_4^*\cos\theta_4^* = u_4 + iv_4,$$

$$r_{23p} = \rho_{23p}\exp\{i\phi_{23p}\}, \quad r_{23} = \rho_{23s}\exp\{i\phi_{23s}\},$$

$$r_{34p} = \rho_{34p}\exp\{i\phi_{34p}\}, \quad r_{34s} = \rho_{34s}\exp\{i\phi_{34s}\}$$

Also, $\alpha$ is a factor represented in relation to $2\beta_3^*$ as follows.

$$2\beta_3^* = \alpha(u_3 + iv_3)$$

From the equations (52-1) to (52-4), the factors $\rho_{23p}$, $\rho_{23s}$, $\rho_{34p}$, $\rho_{34s}$, $\phi_{23p}$, $\phi_{23s}$, $\phi_{34p}$, $\phi_{34s}$, can be given as follows.

$$\rho_{23p}^2 = \{[n_3^2(1 - k_3^2)\cos\theta_2 - n_2u_3]^2 + [2n_3^2k_3\cos\theta_2 - n_2v_3]^2\}/\{[n_3^2(1 - k_3^2)\cos\theta_2 + n_2u_3]^2 + [2n_3^2k_3\cos\theta_2 + n_2v_3]^2\} \qquad (65)$$

$$\rho_{23s}^2 = [\{n_2\cos\theta_2 - u_3\}^2 + v_3^2]/[\{n_2\cos\theta_2 + u_3\}^2 + v_3^2] \qquad (66)$$

$$\rho_{34p}^2 = [\{q_1q_3 + q_2q_4\}^2 + \{q_2q_3 - q_1q_4\}^2]/\{q_3^2 + q_4^2\}^2 \qquad (67)$$

$$\rho_{34s}^2 = [(u_3^2 - u_4^2 + v_3^2 - v_4^2)^2 + 4(u_4v_3 - u_3v_4)^2]/ \qquad (68)$$
$$[(u_3 + u_4)^2 + (v_3 + v_4)^2]^2$$

$$\tan \phi_{23p} = 2n_2n_3^2\cos\theta_2[2k_3u_3 - (1 - k_3^2)v_3]/ \qquad (69)$$
$$[n_3^4(1 + k_3^2)^2\cos^2\theta_2 - n_2^2(u_3^2 + v_3^2)]$$

$$\tan \phi_{23s} = 2v_3n_2\cos\theta_2/[u_3^2 + v_3^2 - n_2^2\cos^2\theta_2] \qquad (70)$$

$$\tan \phi_{34p} = [q_2q_3 - q_1q_4]/[q_1q_3 + q_2q_4] \qquad (71)$$

$$\tan \phi_{34s} = 2(u_4v_3 - u_3v_4)/[u_3^2 - u_4^2 + v_3^2 - v_4^2] \qquad (72)$$

in which $$q_1 = n_4^2(1 - k_4^2)u_3 - n_3^2(1 - k_3^2)u_4 - 2n_4^2k_4v_3 + 2n_3^2k_3v_4$$

$$q_2 = 2n_4^2k_4u_3 + n_4^2(1 - k_4^2)v_3 - 2n_3^2k_3u_4 - n_3^2(1 - k_3^2)v_4$$

$$q_3 = n_4^2(1 - k_4^2)u_3 + n_3^2(1 - k_3^2)u_4 - 2n_4^2k_4v_3 - 2n_3^2k_3v_4$$

$$q_4 = 2n_4^2k_4u_3 + n_4^2(1 - k_4^2)v_3 + 2n_3^2k_3u_4 + n_3^2(1 - k_3^2)v_4$$

$$2u_3^2 = n_3^2(1 - k_3^2) - n_1^2\sin^2\theta_1 + \sqrt{(n_3^2(1 - k_3^2) - n_1^2\sin^2\theta_1)^2 + 4n_3^4k_3^2}$$

$$2v_3^2 = n_3^2(1 - k_3^2) - n_1^2\sin^2\theta_1 + \sqrt{(n_3^2(1 - k_3^2) - n_2^2\sin^2\theta_2)^2 + 4n_3^4k_3^2}$$

$$2u_4^2 = n_4^2(1 - k_4^2) - n_1^2\sin^2\theta_1 + \sqrt{(n_4^2(1 - k_4^2) - n_1^2\sin^2\theta_1)^2 + 4n_4^4k_4^2}$$

$$2v_3^2 = -n_4^2(1 - k_4^2) + n_1^2\sin^2\theta_1 + \sqrt{(n_4^2(1 - k_4^2) - n_1^2\sin^2\theta_1)^2 + 4n_4^4k_4^2}$$

From the equations (59) and (60), representing $\delta_p - \delta_s$ by the functions $\eta_p$ and $\eta_s$, we have the following equation $$\cos^{-1}\{\eta_p(n_1, n_2, n_3, k_3, n_4, k_4, d_3, \theta_1, \lambda, R_p)\} - \qquad (73)$$
$$\cos^{-1}\{\eta_s(n_1, n_2, n_3, k_3, n_4, k_4, d_3, \theta_1, \lambda, R_s)\} = \delta_p - \delta_s$$

The functions $\delta_p - \delta_s$ can also be represented as follows from the equations (61) and 62).

$$\dot{\delta}_p - \delta_s = \tan^{-1}\{\xi_p(n_1, n_2, n_3, k_3, n_4, k_4, d_3, \theta_1, \lambda)\} - \qquad (74)$$
$$\tan^{-1}\{\xi_s(n_1, n_2, n_3, k_3, n_4, k_4, d_3, \theta_1, \lambda)\}$$

The functions $\eta_p$, $\eta_s$, $\xi_p$ and $\xi_s$ are not so simple. However, it is essentially possible to calculate the functions by calculating each factor of the definition equation (59) to (62) as a function of essential variables $\lambda$, $\theta_1$, $n_1$, $n_2$, $n_3$, $k_3$, $d_3$, $n_4$, $k_4$ $R_p$ and $R_s$. The calculation sequence may be preprogrammed in a computer.

Of the above variables $\lambda$, $\theta_1$, $n_1$, $n_2$, $n_3$, $k_3$, $d_3$, $n_4$, $k_4$, $R_p$ and $R_s$, the variables $n_1$, $n_3$, $k_3$, $d_3$, $n_4$ and $k_4$ are known. Also, $\lambda$ is specified as a constant wavelength of the laser emitted from the light source. The incident angle $\theta_1$ is specified as one of conditions of the measurement. $R_p$ and $R_s$ are determined by the measurement.

Each function becomes a function of only one variable $n_2$, $\eta_p(n_2)$, $\eta_s(n_2)$ and $\xi_p(n_2)$ and $\xi_s(n_2)$. Therefore, from equations (73) and (74)

$$\cos^{-1}\{\eta_p(n_2)\} - \cos^{-1}\{\eta_s(n_2)\} = \tan^{-1}\{\xi_p(n_2)\} - \tan^{-1}\{\xi_s(n_2)\} \qquad (A)$$

The value of $n_2$ which satisfies the equation (A) is the genuine refractive index of the uppermost thin film and it can be obtained by a numerical search. For example, the equation (A) can be solved by calculating the right side and the left side of the equation (A), individually, changing the variable $n_2$ as a parameter by a minute step, and seeking the value of the parameter $n_2$ which satisfies the calculated right side and the left side of the equation (A).

Then, representing $2\beta_2$ by the functions $\eta_p$ and $\eta_s$, from the equations (59) and (61), $2\beta_2$ is represented as by the functions $$2\beta_2 = \cos^{-1}\{\eta_p(n_1, n_2, n_3, k_3, n_4, k_4, d_3, \theta_1, \lambda, R_p)\} - \qquad (75)$$
$$\tan^{-1}\{\xi_p, (n_1, n_2, n_3, k_3, n_4, k_4, d_3, \theta_1, \lambda)\}$$

Also, from the equation (60) and (62), $2\beta_2$ is represented as $$2\beta_2 = \cos^{-1}\{\eta_s(n_1, n_2, n_3, k_3, n_4, k_4, d_3, \theta_1, \lambda, R_s)\} - \qquad (76)$$
$$\tan^{-1}\{\xi_s, (n_1, n_2, n_3, k_3, n_4, k_4, d_3, \theta_1, \lambda,)\}$$

$n_1$, $n_3$, $k_3$, $n_4$, $k_4$, $d_3$ $\theta_1$, $\lambda$ are known values and $R_p$ and $R_s$ are the measured values and therefore the only unknown parameter $n_2$ in the functions $\eta_p$, $\eta_s$, $\xi_p$, $\xi_s$, and from equations (75) and (76)

$$\cos^{-1}\{\eta_p(n_2)\} - \tan^{-1}\{\xi_p(n_2)\} = \cos^{-1}\{\eta_s(n_2)\} - \tan^{-1}\{\xi_s(n_2)\} \qquad (B)$$

The refractive index $n_2$ of the uppermost thin film can be determined from $n_2$ which satisfies the equation (B), in accordance with the calculation process mentioned above.

Although the above explanation refers to an example in which two layers 111 and 112 of thin film are formed on the substrate 113, it is easy to apply the method of the present invention to a structure in which three or more thin film layers are formed on a substrate.

In that case, if the refractive index $n_s^*$ of the substrate considering the absorption coefficient thereof and refractive indices $n_3^* \ldots n_m^*$ (in which m is an integral number and equal to or more than three) of the thin films other than the uppermost thin film as well as the thickness $d_3 \ldots d_m$ thereof are known, and the above mentioned functions $\eta_p$, $\eta_s$, $\xi_p$, $\xi_s$ are specified as a function with regard to only one variable $n_2$ as follows.

$$\eta_p(\lambda, \theta_1, n_1, n_2, n_3^*, n_4^* \ldots n_m^*, d_3 \ldots d_m, n_s^*, R_p)$$
$$\eta_s(\lambda, \theta_1, n_1, n_2, n_3^*, n_4^* \ldots n_m^*, d_3 \ldots d_m, n_s^*, R_s)$$
$$\xi_p(\lambda, \theta_1, n_1, n_2, n_3^*, n_4^* \ldots n_m^*, d_3 \ldots d_m, n_s^*)$$
$$\xi_s(\lambda, \theta_1, n_1, n_2, n_3^*, n_4^* \ldots n_m^*, d_3 \ldots d_m, n_s^*);$$

Therefore, the refractive index of the uppermost thin film can be determined from $n_2$ which satisfies the equation $$\cos^{-1}\{\eta_p(n_2)\} - \cos^{-1}\{\eta_s(n_2)\} = \tan^{-1}\{\xi_p(n_2)\} - \tan^{-1}\{\xi_s(n_2)\} \qquad (A)$$

or the equation $$\cos^{-1}\{\eta_p(n_2)\} - \tan^{-1}\{\xi_p(n_2)\} = \cos^{-1}\{\eta_s(n_2)\} - \tan^{-1}\{\xi_s(n_2)\} \qquad (B)$$

The measuring method according to the fourth embodiment of the present invention can be carried out with the use of the apparatus of FIG. 10. An experimental result of the measurement according to the fourth embodiment is described below. As mentioned before, in FIG. 10, reference numerals 131 and 132 designate an He - Ne laser source which emits a stabilized laser beam of wavelength 6328 Å. A polarizer 144,145 is disposed in front of each of the light sources 131 and 132 so as to obtain an S-polarized light and a P-polarized light from the light sources. The S and P-polarized light can be selected by changing shutters 143A and 143B so as to selectively irradiate the sample 0 to be measured through a polarization beam splitter 146 having a high extinction ratio.

The sample 0 and a photodetector 147 are disposed on a table 148a and an arm 148b of $\theta - 2\theta$ rotation system 148, respectively, as illustrated in the drawing. The $\theta - 2\theta$ rotation system 148 functions in a manner that when the table 148a on which the sample 0 is placed rotates by an angle $\theta$, the arm 148b which supports the photodetector 147 rotates an angle $2\theta$ in the same direction as the table. Thereby, it is possible to detect the light reflected from the sample 0 by the photodetector 147 for any incident angle of the light to the sample 0 within a range between 0 and 90 degrees.

The output from the photodetector 147 is input to the data processing system 138 which comprises a computer which carries out the above mentioned calculation processes in which the functions $\eta_p$ and $\eta_s$ or $\xi_p$ and $\xi_s$ are specified as a function of $n_2$, and in which, using the equation (A) or (B), $n_2$ is determined.

The sample comprises a silicon (Si) substrate having a refractive index 3.858 (1+0.00476i), an SiN film having a refractive index 2.0(1+0.001i) and thickness 5000 Å formed on the substrate by plasma CVD process and an uppermost SiO film formed on the SiN film by sputtering process. The uppermost $SiO_2$ film is an object of the measurement.

The sample is set on the apparatus of FIG. 10 in which the incident angle $\theta_1$ is arranged for 60 degrees. By selectively opening and closing the shutters 143A and 143B, P-polarized light and S-polarized light are selectively irradiated to the sample and the reflectances $R_p$ and $R_s$ are measured by detecting the luminous intensity of the reflected light from the sample by the photodetector 147. The result of the measurement is as follows.

$R_p = 0.0854553$
$R_s = 0.369958$

Then, substituting the measurement results, the refractive index of the substrate, the refractive index and thickness of the SiN film, the wavelength of the light and the angle of incidence of the light to the sample into the equation (B), the value of $n_2$ was determined. More particularly, value of the parameter $n_2$ is varied from 1.4 to 1.5 by steps of every 0.001 (the amount of a step can be selected as desired) so as to calculate the $\cos^{-1}\{\eta_p(n_2)\} - \tan^{-1}\{\xi_p(n_2)\}$ and $\cos^{-1}\{\eta_s(n_2)\} - \tan^{-1}\{\xi_s(n_2)\}$ for each step of the parameter $n_2$. The result of the calculation is represented in FIG. 14.

Figure 14:
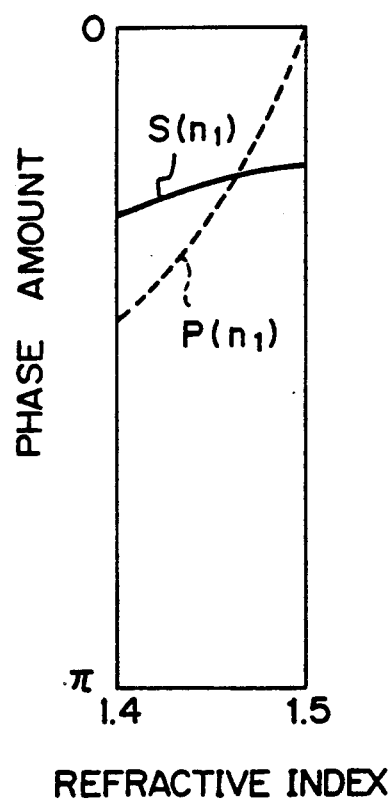
FIG. 14 is a graphical view showing a result of the measuring method according to the fourth embodiment of the present invention.

As can be seen from FIG. 14, the equation (B) is satisfied when $n_2 = 1.460$. Therefore, the refractive index of the $SiO_2$ thin film is determined as 1.460.

As mentioned above, the fourth embodiment of the present invention also provides a novel method for measuring refractive index of thin film in which the refractive index of an uppermost thin film of a multi-layered thin film can be readily measured noncontactingly and nondestructively in high accuracy.

Many widely different embodiments of the present invention may be constructed without departing from the spirit and scope of the present invention. It should be understood that the present invention is not limited to the specific embodiments described in this specification, except as defined in the appended claims.

What is claimed is:

1. A method for measuring a refractive index of an uppermost thin film of multilayered thin films formed on a substrate comprising the steps of:
    (a) irradiating a P-polarized monochromatic light and an S-polarized monochromatic light on said multilayered thin films at a predetermined angle of incidence;
    (b) measuring intensities of said P-polarized and S-polarized monochromatic lights reflected on said multilayered thin films;
    (c) determining respectively a reflectance $R_p$ of said reflected P-polarized monochromatic light and a reflectance $R_s$ of said reflected S-polarized monochromatic light on the basis of said measured intensities of said P-polarized and S-polarized monochromatic lights;
    (d) determining a phase change $2\beta_p$ of said irradiated P-polarized monochromatic light, which phase change $2\beta_p$ is caused during double transversals of said irradiated P-polarized monochromatic light in said uppermost thin film, as a function of said refractive index of said uppermost thin film $n_2$ by using a known wavelength of said P-polarized monochromatic light $\lambda$, said predetermined angle of incidence $\theta_1$ a known refractive index of said substrate $n_s$, known refractive indices of thin films other than said upper most thin film $n_3, n_4 \ldots n_m$, known thicknesses of said films other than said uppermost thin film $d_3, d_4 \ldots d_m$, and said determined reflectance $R_p$, to thereby obtain a function of $2\beta_p = P(n_2)$;
    (e) determining a phase change $2\beta_s$ of said irradiated S-polarized monochromatic light, which phase change $2\beta_s$ is caused during double traversals of said irradiated S-polarized monochromatic light in said uppermost thin film, as a function of said refractive index of said uppermost thin film $n_2$ by using said wavelength $\lambda$, said predetermined angle of incidence $\theta_1$, said refractive index $n_s$, said refractive indices $n_3, n_4 \ldots n_m$, said thicknesses $d_3, d_4 \ldots d_m$ and said determined reflectance $R_s$, to thereby obtain a function of $2\beta_s = S(n_2)$; and
    (f) determining a value of $n_2$ which satisfies the following equation as a value of said refractive index of said uppermost thin film, $P(n_2) = S(n_2)$.

2. An apparatus for measuring a refractive index of an uppermost thin film of multilayered thin films formed on a substrate comprising:
    means for irradiating a P-polarized monochromatic light and an S-polarized monochromatic light on said multilayered thin films at a predetermined angle of incidence;
    light detecting means disposed on an optical path of said P-polarized and S-polarized monochromatic lights for receiving said P-polarized and S-polarized monochromatic lights reflected on said multilayered thin films, and for issuing respectively a first signal representing an intensity of said received P-polarized monochromatic light and a second signal representing an intensity of said received S-polarized monochromatic light; and
    calculation means electrically connected to said light detecting means for receiving said first and second signals to thereby determine a reflectance $R_p$ of said P-polarized monochromatic light and a reflectance $R_s$ of said S-polarized monochromatic light on the basis of said received first and second signals, for determining a phase change $2\beta_p$ of said irradiated P-polarized monochromatic light, which phase change $2\beta_p$ is caused during double transversals of said irradiated P-polarized monochromatic light in uppermost thin film, as a function of said refractive index of said uppermost thin film $n_2$ by using a known wavelength of said P-polarized monochromatic light $\lambda$, said predetermined angle of incidence $\theta_1$, a known refractive index of said substrate $n_s$, known refractive indices of thin films other than said uppermost thin film $n_3, n_4 \ldots n_m$, known thicknesses of said thin films other than said uppermost thin film $d_3, d_4 \ldots d_m$, and said determined reflectance $R_p$, to thereby obtain a function of $2\beta_p = P(n_2)$, for determining a phase change $2\beta_s$ of said irradiated S-polarized monochromatic light, which phase change $2\beta_s$ is caused by during double traversals of said irradiated S-polarized monochromatic light in said uppermost thin film, as a function of said refractive index of said uppermost thin film $n_2$ by using said wavelength $\lambda$, said predetermined angle of incidence $\theta_1$, said refractive index $n_s$, said refractive indices $n_3, n_4 \ldots n_m$, said thicknesses of $d_3, d_4 \ldots d_m$ and said predetermined reflectance $R_s$, to thereby obtain a function of $2\beta_s = S(n_2)$, and for determining a value of $n_2$ which satisfies the following equation as a value of said refractive index of said uppermost thin film, $P(n_2) = S(n_2)$.

* * * * *